(12) United States Patent
Falwell et al.

(10) Patent No.: US 9,750,567 B2
(45) Date of Patent: *Sep. 5, 2017

(54) ELECTROPHYSIOLOGY CATHETER FOR MAPPING AND/OR ABLATION

(71) Applicant: Boston Scientific Scimed, Inc., Maple Grove, MN (US)

(72) Inventors: Gary S. Falwell, Wilmington, MA (US); Steven J. Burns, Haverhill, MA (US); Charles A. Gibson, Malden, MA (US); David MacAdam, Millbury, MA (US); Nickolas G. Davis, Bradford, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 289 days.

This patent is subject to a terminal disclaimer.

(21) Appl. No.: 14/143,135

(22) Filed: Dec. 30, 2013

(65) Prior Publication Data

US 2014/0107644 A1 Apr. 17, 2014

Related U.S. Application Data

(60) Continuation of application No. 13/487,907, filed on Jun. 4, 2012, now Pat. No. 8,636,731, which is a continuation of application No. 11/974,340, filed on Oct. 12, 2007, now Pat. No. 8,206,384, which is a division of application No. 10/475,942, filed as application No. PCT/US02/10101 on Mar. 29, 2002, now Pat. No. 7,300,438.

(60) Provisional application No. 60/345,119, filed on Oct. 19, 2001, provisional application No. 60/287,057, filed on Apr. 27, 2001.

(51) Int. Cl.
A61B 18/14 (2006.01)
A61B 18/18 (2006.01)
A61B 18/00 (2006.01)

(52) U.S. Cl.
CPC ...... *A61B 18/1492* (2013.01); *A61B 18/1815* (2013.01); *A61B 2018/00839* (2013.01); *A61B 2018/1435* (2013.01)

(58) Field of Classification Search
CPC ........ A61B 18/1492; A61B 2018/1407; A61B 2018/1435
See application file for complete search history.

(56) References Cited

U.S. PATENT DOCUMENTS

| 4,998,923 A | 3/1991 | Samson et al. |
| 5,195,968 A | 3/1993 | Lundquist et al. |
| 5,242,394 A | 9/1993 | Tremulis |

(Continued)

FOREIGN PATENT DOCUMENTS

| DE | 3819372 C1 | 1/1990 |
| EP | 0790066 A2 | 8/1997 |

(Continued)

*Primary Examiner* — Michael Peffley
(74) *Attorney, Agent, or Firm* — Faegre Baker Daniels LLP

(57) ABSTRACT

The present invention encompasses apparatus and methods for mapping electrical activity within the heart. The present invention also encompasses methods and apparatus for creating lesions in the heart tissue (ablating) to create a region of necrotic tissue which serves to disable the propagation of errant electrical impulses caused by an arrhythmia.

20 Claims, 15 Drawing Sheets

(56) References Cited

U.S. PATENT DOCUMENTS

| | | |
|---|---|---|
| 5,322,064 A | 6/1994 | Lundquist |
| 5,327,905 A | 7/1994 | Avitall |
| 5,329,923 A | 7/1994 | Lundquist |
| 5,334,168 A | 8/1994 | Hemmer |
| 5,354,297 A | 10/1994 | Avitall |
| 5,358,478 A | 10/1994 | Thompson et al. |
| 5,383,852 A | 1/1995 | Stevens et al. |
| 5,437,282 A | 8/1995 | Koger et al. |
| 5,449,343 A | 9/1995 | Samson et al. |
| 5,462,527 A | 10/1995 | Stevens et al. |
| 5,545,200 A | 8/1996 | West et al. |
| 5,558,643 A | 9/1996 | Samson et al. |
| 5,596,996 A | 1/1997 | Johanson et al. |
| 5,611,777 A | 3/1997 | Bowden et al. |
| 5,626,136 A * | 5/1997 | Webster, Jr. ......... A61B 5/0422 600/373 |
| 5,642,736 A | 7/1997 | Avitall |
| 5,643,231 A | 7/1997 | Lurie et al. |
| 5,680,860 A | 10/1997 | Imran |
| 5,755,760 A * | 5/1998 | Maguire ............... A61B 5/0422 607/122 |
| 5,782,900 A * | 7/1998 | de la Rama ....... A61B 18/1492 600/374 |
| 5,820,591 A | 10/1998 | Thompson et al. |
| 5,836,947 A * | 11/1998 | Fleischman ........ A61B 18/1492 606/41 |
| 5,843,076 A * | 12/1998 | Webster, Jr. ....... A61B 18/1492 600/439 |
| 5,865,800 A | 2/1999 | Mirarchi et al. |
| 5,916,178 A | 6/1999 | Noone et al. |
| 5,931,811 A | 8/1999 | Haissaguerre et al. |
| 5,938,694 A * | 8/1999 | Jaraczewski ......... A61B 5/0422 600/373 |
| 5,957,961 A | 9/1999 | Maguire et al. |
| 6,074,351 A | 6/2000 | Houser et al. |
| 6,099,524 A | 8/2000 | Lipson et al. |
| 6,126,654 A | 10/2000 | Giba et al. |
| 6,178,354 B1 * | 1/2001 | Gibson ............... A61B 18/1492 607/116 |
| 6,217,567 B1 | 4/2001 | Zadno-Azizi et al. |
| 6,241,727 B1 | 6/2001 | Tu et al. |
| 6,245,066 B1 | 6/2001 | Morgan et al. |
| 6,278,563 B1 | 8/2001 | Hewlett |
| 6,308,090 B1 | 10/2001 | Tu et al. |
| 6,315,778 B1 | 11/2001 | Gambale et al. |
| 6,325,797 B1 | 12/2001 | Stewart et al. |
| 6,375,628 B1 | 4/2002 | Zadno-Azizi et al. |
| 6,447,506 B1 | 9/2002 | Swanson et al. |
| 6,592,581 B2 | 7/2003 | Bowe |
| 6,607,520 B2 | 8/2003 | Keane |
| 6,616,628 B2 | 9/2003 | Hayzelden |
| 6,728,563 B2 * | 4/2004 | Rashidi ............... A61B 18/1492 600/374 |
| 6,771,996 B2 | 8/2004 | Bowe et al. |
| 6,804,545 B2 | 10/2004 | Fuimaono et al. |
| 7,300,438 B2 | 11/2007 | Falwell et al. |
| 8,206,384 B2 | 6/2012 | Falwell et al. |
| 8,636,731 B2 | 1/2014 | Falwell et al. |
| 2001/0025134 A1 | 9/2001 | Bon et al. |

FOREIGN PATENT DOCUMENTS

| | | |
|---|---|---|
| EP | 1199082 A1 | 4/2002 |
| JP | 05265684 A | 4/1995 |
| JP | 10189489 A | 1/2000 |
| WO | 9707848 A1 | 3/1997 |
| WO | 9742996 A1 | 11/1997 |
| WO | 0101877 | 1/2001 |
| WO | 0137723 A2 | 5/2001 |
| WO | 02094334 A1 | 11/2002 |

* cited by examiner

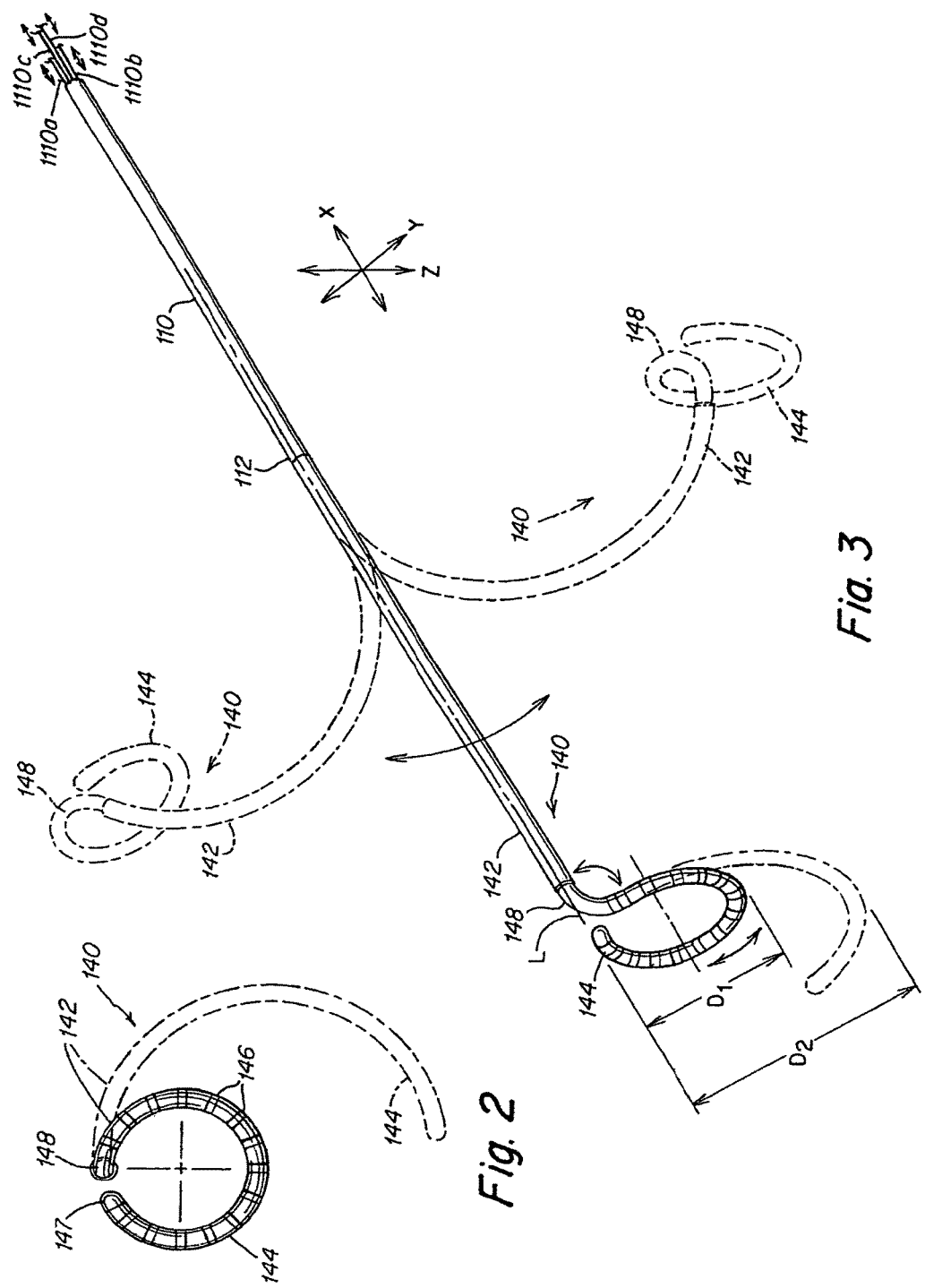

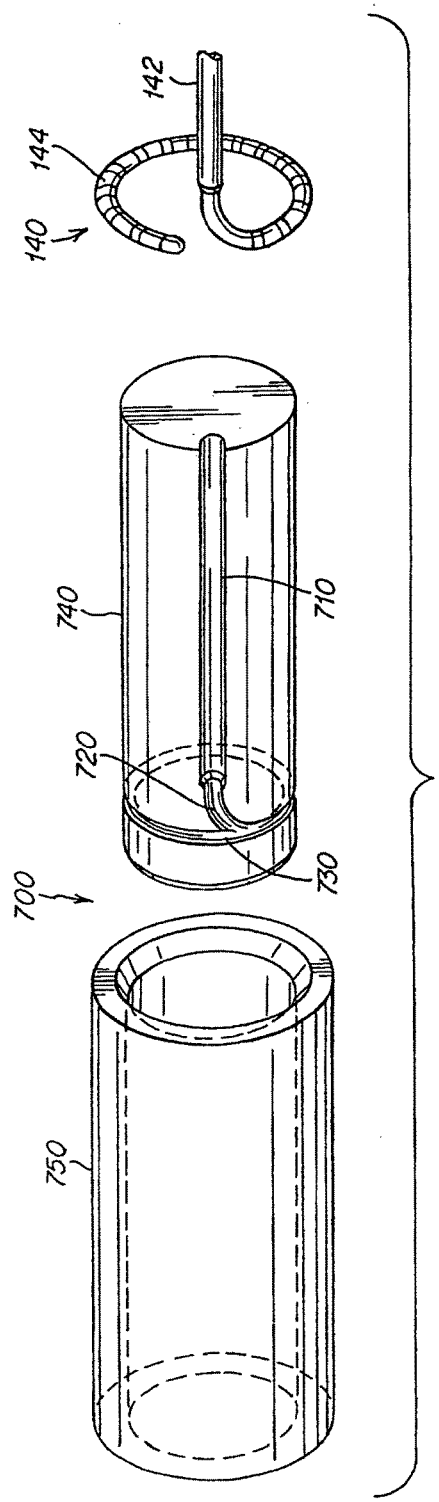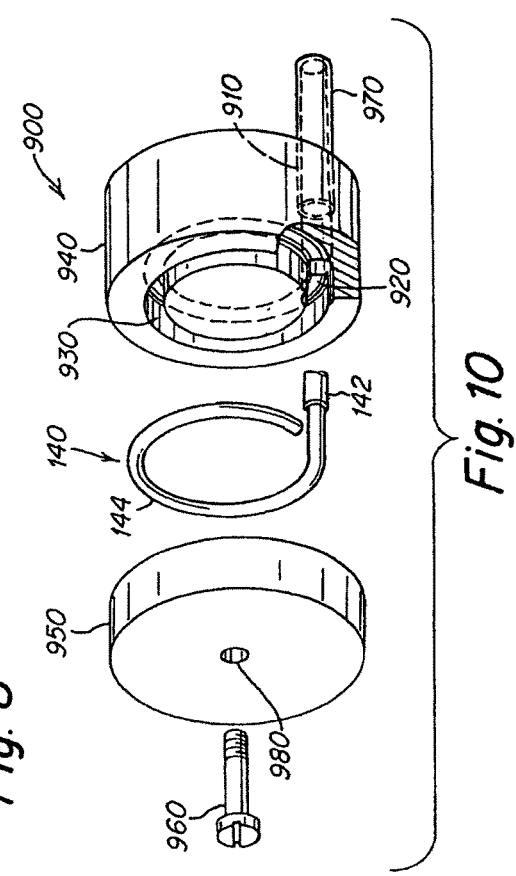

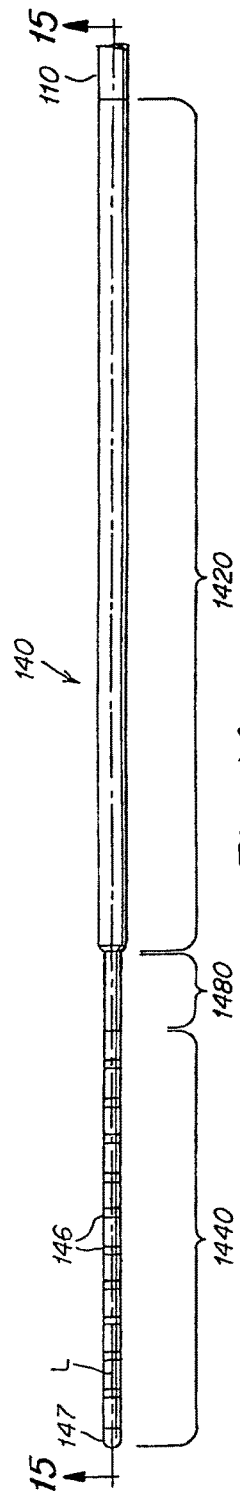
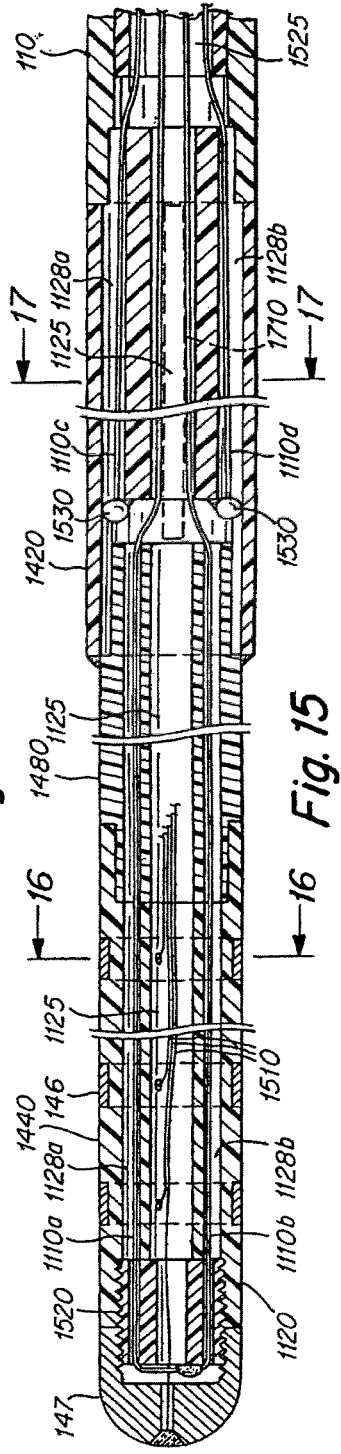
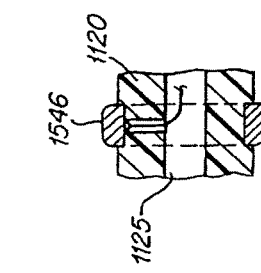
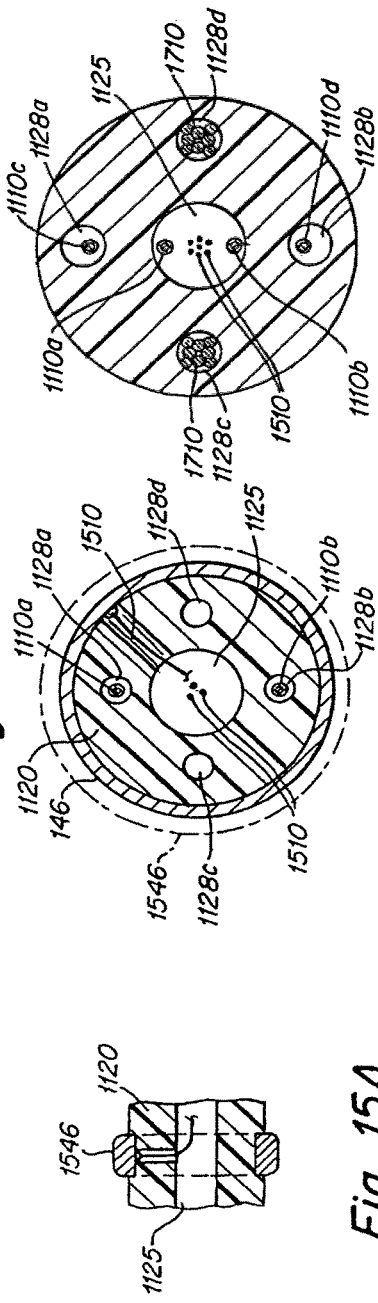
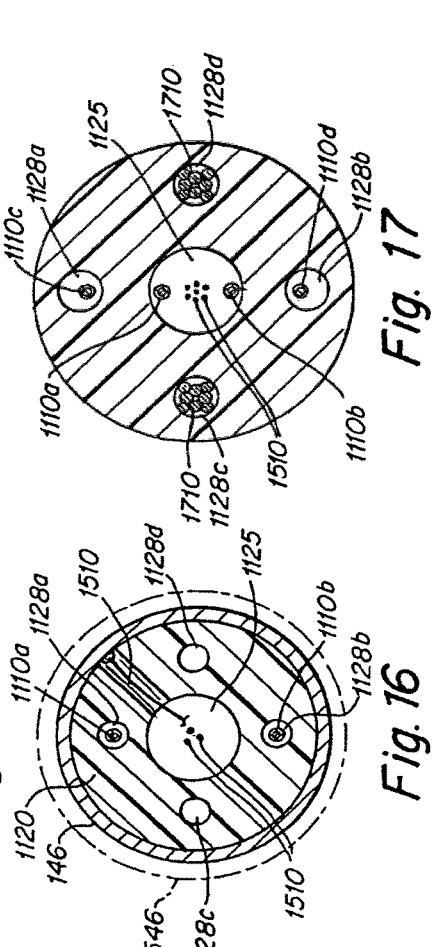

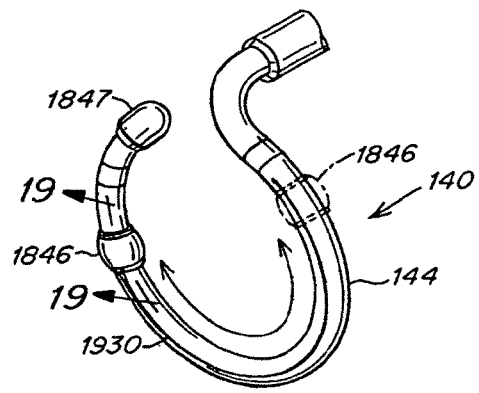
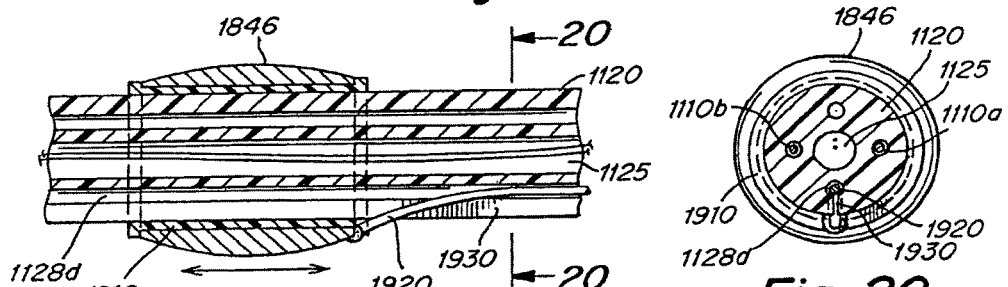
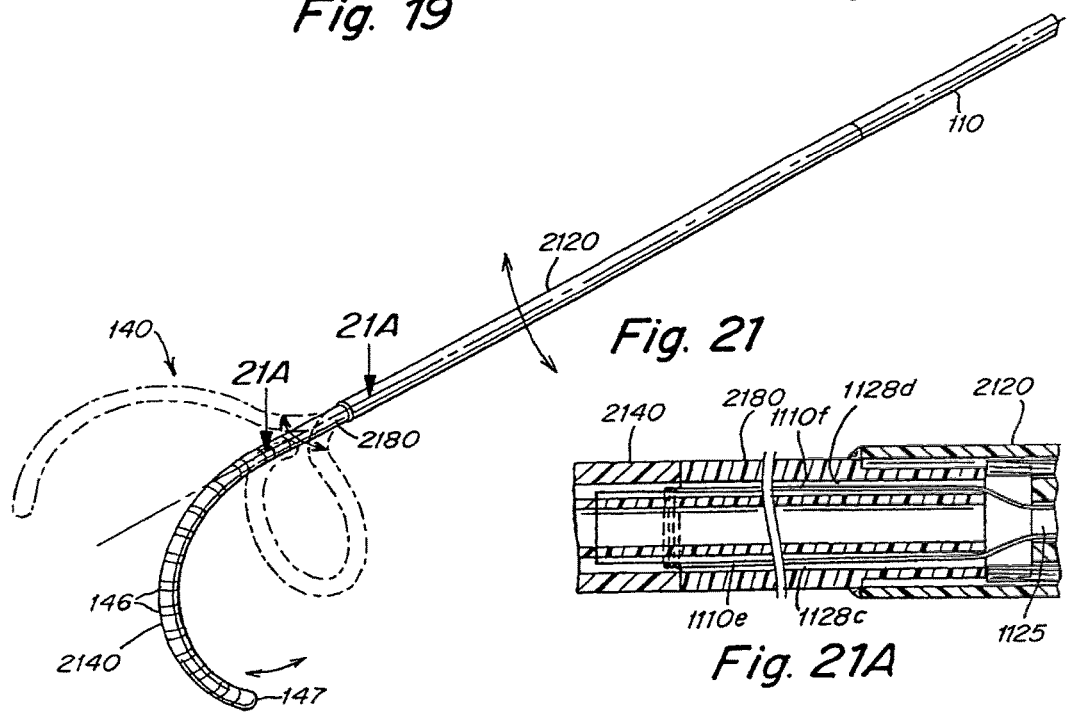

ELECTROPHYSIOLOGY CATHETER FOR MAPPING AND/OR ABLATION

CROSS REFERENCE TO RELATED APPLICATIONS

The present application claims the benefit under 35 U.S.C. §120 as a continuation of U.S. patent application Ser. No. 13/487,907, entitled "Electrophysiology Catheter for Mapping and/or Ablation," filed on Jun. 4, 2012, now U.S. Pat. No. 8,636,731, which is a continuation of U.S. patent application Ser. No. 11/974,340, entitled "Electrophysiology Catheter for Mapping and/or Ablation," filed on Oct. 12, 2007, now U.S. Pat. No. 8,206,384, which is a divisional of U.S. patent application Ser. No. 10/475,942, entitled "Electrophysiology Catheter For Mapping and/or Ablation," filed on May 10, 2004, now U.S. Pat. No. 7,300,438, which is a national stage application claiming the benefit under 35 U.S.C. §371 of International Application No. PCT/US2002/10101, entitled "Electrophysiology Catheter For Mapping and/or Ablation," filed on Mar. 29, 2002, which claims the benefit under 35 U.S.C. §119(e) of U.S. Provisional Application Nos. 60/287,057, entitled "Handles for Medical Devices," filed on Apr. 27, 2001, and 60/345,119, entitled "Handle Thumb Wheel Mechanism Which Maintains Holding Forces When Sterilized," filed on Oct. 19, 2001, all of which are hereby incorporated by reference in their entirety.

BACKGROUND OF THE INVENTION

1. Field of the Invention

The present invention relates to electrophysiology catheters, and more particularly to electrophysiology catheters for performing endocardial mapping and/or ablation procedures.

2. Discussion of the Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel and into an endocardial site, and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

SUMMARY OF THE INVENTION

The present invention encompasses apparatus and methods for mapping electrical activity within the heart. The present invention also encompasses methods and apparatus for creating lesions in the heart tissue (ablating) to create a region of necrotic tissue which serves to disable the propagation of errant electrical impulses caused by an arrhythmia.

According to one aspect of the present invention, an electrophysiology catheter is provided. In one embodiment, the catheter comprises a handle, a flexible shaft, a tip assembly, and a cable. The handle has a distal end and a proximal end and includes an actuator. The flexible shaft has a proximal end and a distal end and a longitudinal axis that extends along a length of the shaft, the proximal end of the shaft being attached to the distal end of the handle. The tip assembly has a proximal end and a distal end, the proximal end of the tip assembly being attached to the distal end of the shaft. The distal end of the tip assembly is biased in an arcuately curved shape having a radius of curvature. The cable is attached to the actuator and the distal end of the tip assembly and extends through the shaft. The cable is adapted to change the radius of curvature of the distal end of the tip assembly in response to movement of the actuator.

According to another embodiment of the present invention, an electrophysiology catheter is provided that comprises a handle, a flexible shaft, a tip assembly, and a cable. The handle has a distal end and a proximal end and includes an actuator. The flexible shaft has a proximal end and a distal end and a longitudinal axis that extends along a length of the shaft, the proximal end of the shaft being attached to the distal end of the handle. The tip assembly has a proximal end and a distal end, the proximal end of the tip assembly being attached to the distal end of the shaft. The proximal end of the tip assembly includes a fixed bend of approximately ninety degrees relative to the longitudinal axis of the shaft, and the distal end of the tip assembly includes an arcuate curve having a diameter, the arcuate curve being oriented in a plane that is approximately perpendicular to the longitudinal axis of the shaft. The cable is attached to the actuator and the distal end of the tip assembly and extends through the shaft. The cable is adapted to change the diameter of the arcuate curve in response to movement of the actuator.

According to another embodiment of the present invention, an electrophysiology catheter is provided that comprises a handle, a flexible shaft, a tip assembly, and first and second cables. The handle has a distal end and a proximal end and includes a first actuator and a second actuator. The flexible shaft has a proximal end and a distal end and a longitudinal axis that extends along a length of the shaft, the proximal end of the shaft being attached to the distal end of the handle. The tip assembly has a proximal end and a distal end, the proximal end of the tip assembly being attached to the distal end of the shaft and the distal end of the tip assembly being biased in an arcuately curved shape and having a radius of curvature. The first cable is attached to the first actuator and the proximal end of the tip assembly and extends through the shaft. The first cable is adapted to bend the distal end of the tip assembly so that the distal end of the tip assembly is approximately perpendicular to the longitudinal axis of the shaft in response to movement of the first actuator. The second cable is attached to the second actuator and the distal end of the tip assembly and extends through the shaft. The second cable is adapted to change the radius of curvature of the distal end of the tip assembly in a plane that is approximately perpendicular to the longitudinal axis of the shaft in response to movement of the second actuator.

According to another aspect of the present invention, a handle is provided for use with a catheter. In one embodiment the catheter has an elongated shaft and a tip assembly attached to a distal end of the elongated shaft. The shaft has a longitudinal axis that extends along a length of the shaft, and the tip assembly includes at least one cable for changing at least one of a shape of the tip assembly and an orientation of the tip assembly relative to the longitudinal axis of the shaft. The handle comprises a housing and an actuator that is disposed on the housing. The actuator is attached to the at least one cable and movable between a first position defining one of a first shape of the tip assembly and a first orientation of the tip assembly relative to the longitudinal axis of the shaft and a second position defining one of a second shape of the tip assembly and a second orientation of the tip assembly relative to the longitudinal axis of the shaft. The handle further comprises frictional means for imparting a first amount of friction on the at least one cable in the first position and for imparting a second amount of friction on the at least one cable when the actuator is moved away from the first position, the second amount of friction being greater than the first amount of friction.

According to another embodiment of the present invention, a handle for use with a catheter having a proximal end and a distal end is provided. The catheter includes at least one cable for moving a portion of the distal end of the catheter between a first position and a second position relative to the proximal end of the catheter. The handle comprises a housing, an actuator disposed on the housing, the actuator being attached to the at least one cable and movable between a third position and a fourth position. The third position of the actuator corresponds to the first position of the portion of the distal end of the catheter relative to the proximal end of the catheter, and the fourth position corresponds to the second position of the portion of the distal end of the catheter. The handle further includes frictional means for imparting a first amount of friction on the actuator when the actuator is in the third position and for imparting a second amount of friction on the actuator when the actuator is moved away from the third position, the second amount of friction being greater than the first amount of friction.

According to another aspect of the present invention, a handle for use with a catheter having an elongated shaft and a tip assembly attached to a distal end of the elongated shaft is provided. The shaft has a longitudinal axis that extends along a length of the shaft, and the tip assembly includes at least one cable for changing a radius of curvature of a distal end of the tip assembly. The handle comprises a housing, an actuator disposed on the housing, the actuator being attached to the at least one cable and movable between a first position defining a first radius of curvature of the distal end of the tip assembly and a second position defining a second radius of curvature of the distal end of the tip assembly, and graphical indicia indicative of the radius of curvature of the distal end of the tip assembly when the actuator is in at least one of the first position and the second position.

According to a further aspect of the present invention, a handle for use with a catheter having an elongated shaft and a tip assembly attached to a distal end of the elongated shaft is provided. The shaft has a longitudinal axis that extends along a length of the shaft, and the tip assembly includes at least one cable for changing a radius of curvature of a distal end of the tip assembly. The handle comprises a housing, an actuator disposed on the housing, the actuator being attached to the at least one cable and movable between a first position defining a first radius of curvature of the distal end of the tip assembly and a second position defining a second radius of curvature of the distal end of the tip assembly, and a plurality of protrusions, disposed on at least one of the housing and the actuator, to provide tactile feedback to a user when the actuator is moved from the first position.

According to another aspect of the present invention, a method of shaping a distal end of a catheter is provided. The method comprises acts of placing the distal end of the catheter in a jig, maintaining the distal end of the catheter and the jig at a predetermined temperature for a predetermined time, and removing the distal end of the catheter from the jig. The jig includes a passageway to receive the distal end of the catheter and hold the distal end of the catheter in a fixed position. The passageway defines three contiguous regions including a first straight region formed in a first plane, a second curved region in which the passageway bends within the first plane approximately perpendicularly to the first straight region, and a third curved region in which the passageway curves arcuately in a second plane that is perpendicular to the first plane.

According to another aspect of the present invention, a jig for shaping a distal end of a catheter is provided. The jig comprises a mandrel having a passageway to receive the distal end of the catheter, and a retainer removably attached to the mandrel to hold the distal end of the catheter within the passageway. The passageway defines three contiguous regions including a first straight region formed in a first plane, a second curved region in which the passageway bends within the first plane approximately perpendicularly to the first straight region, and a third curved region in which the passageway curves arcuately in a second plane that is perpendicular to the first plane.

According to another aspect of the present invention, a method of using a catheter is provided. The catheter includes a handle, a flexible shaft having a longitudinal axis, and a tip assembly, the shaft being connected between the handle and the tip assembly. A distal end of the tip assembly includes an arcuate curve having a diameter. The method comprises acts of placing the tip assembly inside a heart of a patient, and remotely, from outside the patient, adjusting the diameter of the arcuate curve.

According to another embodiment, a method of using a catheter is provided. The catheter includes a handle, a flexible shaft having a longitudinal axis, and a tip assembly. The shaft is connected between the handle and the tip assembly. A proximal end of the tip assembly includes a fixed bend of approximately ninety degrees relative to the longitudinal axis of the shaft, and the distal end of the tip assembly includes an arcuate curve having a diameter, the arcuate curve being oriented in a plane that is approximately perpendicular to the longitudinal axis of the shaft. The method comprises acts of placing the distal end of the tip assembly inside a heart of a patient so that the arcuate curve of the distal end of the tip assembly contacts an inner surface of a heart vessel, and remotely, from outside the patient, applying a radially outward pressure with the distal end of the tip assembly against the inner surface of the heart vessel.

BRIEF DESCRIPTION OF THE DRAWINGS

Illustrative, non-limiting embodiments of the present invention are described by way of example with reference to the accompanying drawings, in which:

FIG. 2 is an end elevational view of a distal end tip assembly, taken along line 2-2 in FIG. 1, that may be used with the catheter system of FIG. 1 according to one embodiment of the present invention;

FIG. 3 is a perspective view of the distal end tip assembly of FIG. 2;

FIG. 8 is an exploded perspective view of the jig of FIG. 7;

FIG. 9 is a cross sectional side view of a third jig that may be used to impart a fixed shape to the distal end of the tip assembly according to another embodiment of the present invention;

FIG. 10 is an exploded perspective view of the jig of FIG. 9;

FIG. 14 is a side elevational view of the distal end of a finished catheter prior to shaping with any one of the jigs of FIGS. 5-10;

FIG. 15 is a cross sectional view of the distal end of the catheter of FIG. 14 taken along line 15-15 in FIG. 14;

FIG. 15A is a fragmentary cross sectional view of the distal end of the catheter of FIG. 15 showing an alternative raised profile electrode;

FIG. 16 is a cross sectional view of the distal end of the catheter of FIG. 15 taken along line 16-16 in FIG. 15;

FIG. 17 is a cross sectional view of the distal end of the catheter of FIG. 15 taken along line 17-17 in FIG. 15;

FIG. 18 is a perspective view of a distal end tip assembly according to another embodiment of the present invention that may be used with the catheter system of FIG. 1, and which includes a sliding electrode;

FIG. 19 is a cross sectional side view of the distal end tip assembly of FIG. 18 taken along line 19-19 in FIG. 18;

FIG. 20 is a cross sectional end view of the distal end of tip assembly of FIG. 19 taken along line 20-20 in FIG. 19;

FIG. 21 is a perspective view of a distal end tip assembly according to another embodiment of the present invention that may be used with the catheter system of FIG. 1;

FIG. 21A is a cross sectional view of the distal end tip assembly of FIG. 21 taken along line 21A-21A in FIG. 21;

DETAILED DESCRIPTION

In this description, various aspects and features of the present invention will be described. One skilled in the art will appreciate that the features may be selectively combined in a device depending on the particular application. Furthermore, any of the various features may be incorporated in a catheter and associated method of use for mapping and/or ablation procedures.

Catheter Overview

Figure 1:
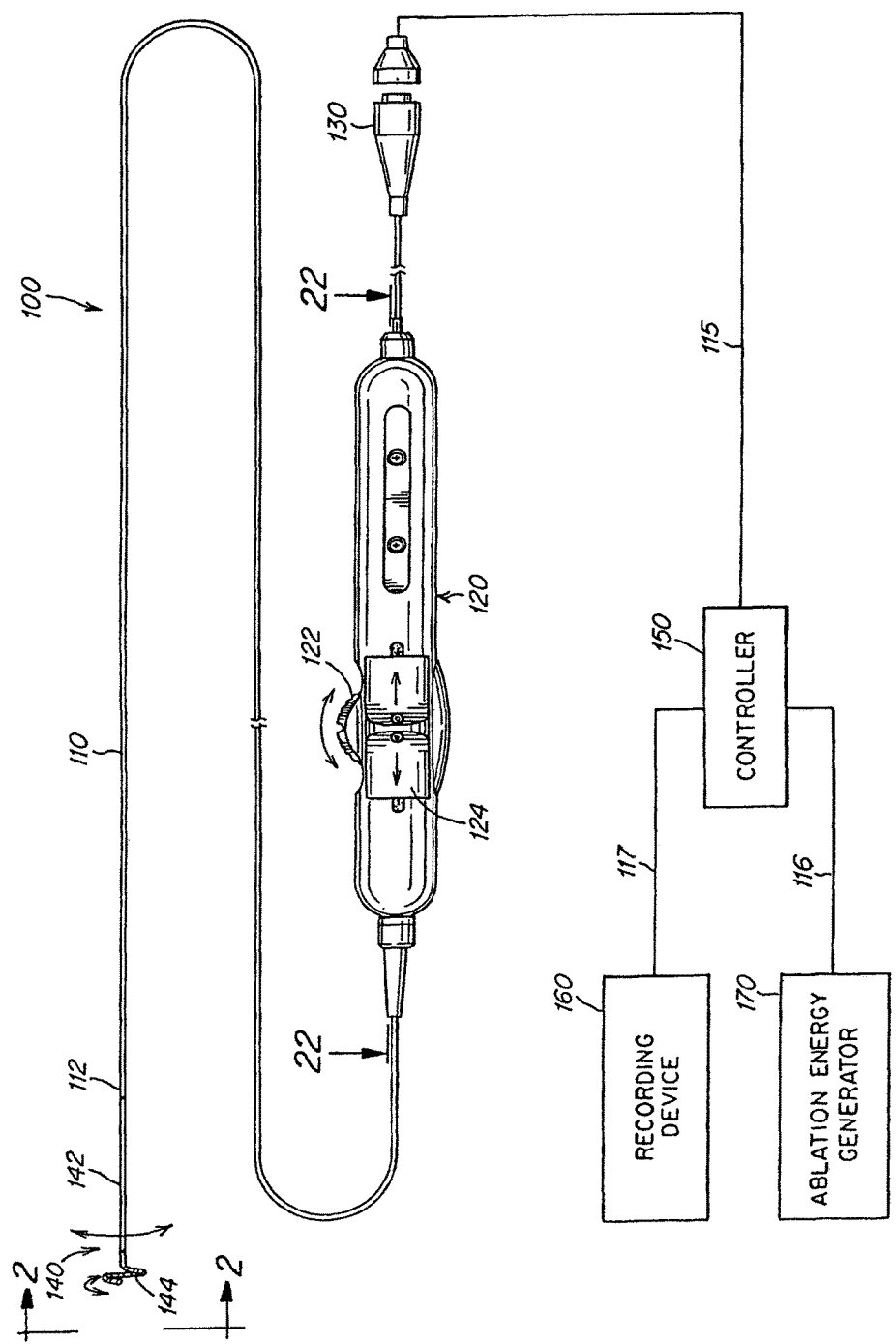
FIG. 1 illustrates a schematic view of a mapping and/or ablation catheter system in accordance with the present invention.

Reference is now made to FIG. 1, which illustrates an overview of a mapping and/or ablation catheter system for use in electrophysiology procedures, in accordance with the present invention. The system includes a catheter 100 having a flexible shaft 110, a control handle 120, and a connector 130. When used in mapping applications, the connector 130 is used to allow signal wires running from mapping electrodes at a distal end of the catheter 100 to be connected to a device for recording signals, such as a recording device 160. When used in ablation applications, connector 130 is used to allow signal wires running from ablation electrodes at the distal end of the catheter 100 to be connected to a device for generating ablation energy, such as ablation energy generator 170. As will be described further in detail below, the distal end of the catheter 100 may include separate mapping and/or ablation electrodes, or may alternatively include electrodes that are adapted for both mapping and ablation.

A controller 150 is electrically connected to connector 130 via cable 115. In one embodiment, controller 150 may be a QUADRAPULSE RF CONTROLLER™ device available from C. R. Bard, Inc., Murray Hill, N.J. Ablation energy generator 170 may be connected to controller 150 via cable 116. Recording device 160 may be connected to controller 150 via cable 117. When used in an ablation application, controller 150 is used to control ablation energy, provided by ablation energy generator 170, to catheter 100. When used in a mapping application, controller 150 is used to process signals from catheter 100 and provide these signals to recording device 160. Although illustrated as separate devices, recording device 160, ablation energy generator 170, and controller 150 may be incorporated into a single device. It should further be appreciated that although both ablation energy generator 170 and recording device 160 are illustrated in FIG. 1, either or both of these devices may be incorporated in the catheter system in accordance with the present invention.

The shaft 110 of the catheter 100 is, in one embodiment, approximately six French in diameter, although it should be appreciated that many diameters are possible, and the diameter of shaft 110 may be smaller or larger depending on the particular application and/or combination of features incorporated into the catheter 100. Attached to a distal end 112 of the shaft 110 is a distal end tip assembly 140 having a proximal end 142 that is attached to the distal end 112 of the shaft 110, and a distal end 144 having one or more electrodes 146 (See FIG. 2). The length of the tip assembly 140 may be approximately 7 to 8 cm in length, although other lengths may be suitably employed, as the present invention is not limited to any particular length. Further, and as will be subsequently described, the number and placement of electrodes along the distal end 144 of the tip assembly 140 may vary depending upon the application. For example, for mapping applications, a plurality of low profile electrodes may be preferred, whereas for ablations applications a lesser number of higher profile electrodes may be preferred. Embodiments of the present invention may include as few as one electrode, which may be movably attached to the distal end 144 of the tip assembly 140, or may alternatively include a plurality of fixed electrodes, for example 20 or more, spaced apart along the distal end 142 of the tip assembly 140. Further, the construction of the electrode or electrodes 146 may vary, as known to those skilled in the art.

According to one aspect of the present invention, and as shown in detail in FIG. 3, the proximal end 142 of the tip assembly 140 includes an approximately ninety degree bend 148 relative to a longitudinal axis (L) of the shaft 110, which may be active, or fixed, and the distal end 144 of the tip assembly 140 includes an arcuate curve that is oriented orthogonally to the longitudinal axis of the shaft 110. As used in association with the approximately ninety degree bend 148, the term "active" is herein defined to mean that the portion of the proximal end 142 of the tip assembly 140 where the bend 148 is formed is capable of movement, relative to the longitudinal axis (L) of the shaft 110 between approximately zero degrees and approximately ninety degrees via manipulation of a remotely controlled actuator (e.g., actuators 122, 124 disposed on the handle 120). The term "fixed," as used in association with the approximately ninety degree bend 148, is herein defined to mean that the approximately ninety degree bend 148 is permanently formed in the proximal end 142 of the tip assembly 140, such that the approximately ninety degree bend retains its shape at body temperatures.

According to a further aspect of the present invention, the radius (or alternatively, the diameter) of curvature of the arcuately curved distal end 144 may be adjustable by operation of an actuator (e.g., actuators 122, 124) disposed on the handle 120. The combination of the approximate ninety degree bend followed by an arcuate curve that is adjustable in diameter permits the catheter 100 to be uniquely suited for mapping and/or ablation procedures in difficult endocardial sites, such as, for example, within a blood vessel, such as a pulmonary vein, or an ostium of a blood vessel, such as the ostium of a pulmonary vein. For example, in both mapping and ablation procedures, the approximately ninety degree bend permits pressure, applied to the handle 120, to be translated to the distal end 144 of the tip assembly 142, to thereby urge the distal end 144 of the tip assembly 140 tight against the endocardial site. The adjustable radius of curvature of the arcuate curve can be used to apply an outwardly radial pressure to further force the distal end 144 of the tip assembly 140 tight against the endocardial site, or to adjust to endocardial sites of different diameters (e.g. that of an adult or large animal, or a small child or small animal), or both. This ability to urge the distal end 144 of the tip assembly tight against an endocardial site is advantageous in mapping procedures to better localize the source of the cardiac arrhythmia, and may be used in ablation procedures to focus the ablation energy on the selected endocardial site. Further, because the radius of curvature of the distal end 144 of the tip assembly can be adjusted to different diameters, the catheter may be used with either an adult (or large animal) or a child (or small animal), as "one size fits all." This ability to accommodate a range of sizes can reduce the number of distinctly sized catheters that need to be stocked by the manufacturer or the care provider.

Disposed on the handle 120 are one or more actuators 122, 124 that may be used for a variety of purposes. Each of the actuators 122, 124 is mechanically coupled to at least one cable that extends to the tip assembly 140 and which may be used to change the shape, orientation, or both the shape and orientation of the tip assembly. In the embodiment depicted in FIG. 1, the handle 120 includes two different actuators, a thumbwheel actuator 122 and a slide actuator 124. In one embodiment, the thumbwheel actuator 122 may be used to change the orientation of the tip assembly 140 in two opposing directions, and the slide actuator 124 may be used to enlarge and decrease the radius of curvature of the arcuately curved distal end 144 of the tip assembly 140. As will be described in detail further below, the operation of the actuators 122, 124 may be reversed, such that the thumbwheel actuator 122 is used to control the radius of curvature, and the slide actuator 124 is used to control the orientation of the tip assembly 140 relative to the shaft 110 (e.g., to provide steering). Moreover, as described further in detail below, the present invention is not limited to two distinct control actuators, as embodiments of the present invention may include only a single actuator that controls only one degree of movement (for example, increasing the radius of curvature of the arcuately curved distal end 144), or may include several actuators, each capable of controlling two degrees of movement.

The Tip Assembly

Figure 4:
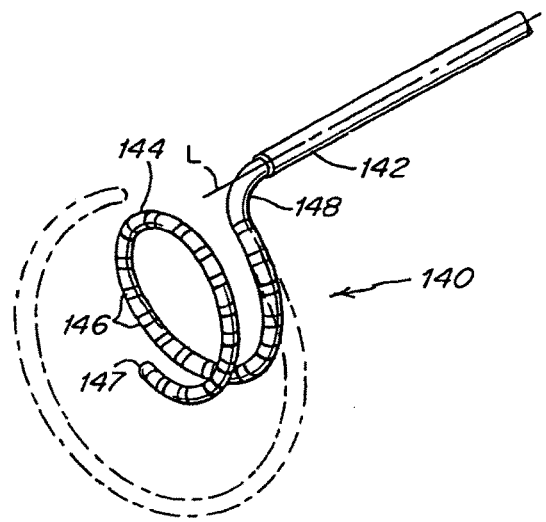
FIG. 4 is an alternative perspective view of the distal end tip assembly of FIG. 2 illustrating the manner in which the radius of curvature of the distal end may be changed.

FIGS. 2-4 illustrate a distal end tip assembly according to one embodiment of the present invention. According to this embodiment, the proximal end 142 of the tip assembly 140 includes an approximately ninety degree bend 148 relative to the longitudinal axis of the shaft 110, followed by an arcuately curved distal end 144. In the embodiment depicted in FIGS. 2-4, the approximately ninety degree bend 148 is fixed, that is, permanently formed in the proximal end 142 of the tip assembly 140, such that the approximately ninety degree bend 148 retains its shape at body temperatures. In other embodiments, the approximately ninety degree bend 148 may be active, that is, movable between approximately zero and approximately ninety degrees relative to the longitudinal axis (L) of the shaft 110 via a pull or push cable attached to one of the actuators 122, 124 on the handle 120, as described further below with respect to FIG. 21.

In each embodiment, the region of the tip assembly 140 that includes the approximately ninety degree bend 148 is preferably biased in a curved position relative to the longitudinal axis (L) of the shaft 110, although the degree of bias may vary. Specifically, in embodiments featuring a fixed bend, the bend 148 is permanently formed in the proximal end 142 of the tip assembly 140 at an angle of approximately ninety degrees, such that while capable of being straightened for introduction into a vessel, such as for example, through the use of a sheath/dilator, the distal end 144 of the tip assembly 140 springs back in its unrestrained state to rest in a plane that is approximately perpendicular to the longitudinal axis (L) of the shaft 110. In embodiments featuring an active bend, only a slight amount of bend, for example, a few degrees, is permanently formed in the proximal end 142 of the tip assembly 140. This slight amount of bend in the proximal end 142 of the tip assembly 140 is sufficient to ensure that the distal end 144 of the tip assembly 140 bends in a predetermined direction relative to the longitudinal axis (L) of the shaft 110, as described more fully below. However, in all embodiments, the distal end 144 of the tip assembly 140 is permanently biased in an arcuate shape to facilitate increases and/or decreases in the radius of curvature of the distal end 144 of the tip assembly 140 in a known and controlled manner.

Disposed on the arcuately curved distal end 144 of the tip assembly 140 are a plurality of ring-shaped electrodes 146 spaced uniformly apart along the distal end 144 and a distal end tip electrode 147. Although illustrated as being uniformly spaced apart on the distal end 144 of the tip assembly 140, the electrodes 146 may alternatively be grouped in pairs, with the distance between each electrode of a pair being closer than the distance between electrodes of adjacent pairs. For example, each ring electrode may be approximately 1 mm in length, with pairs of electrodes being spaced approximately 2 mm apart on center, and with electrodes of adjacent pairs being spaced apart by approximately 8 mm. Furthermore, although the electrodes 146 illustrated in FIG. 2 are shown as being low profile ring electrodes that conform to the surface of the distal end 144 of the tip assembly 140, they may also be raised in profile. Indeed, as described further in detail below, embodiments of the present invention may be used with any type of electrode that is suitable for use in endocardial or epicardial mapping and/or ablation procedures, as the present invention is not limited to the number, the construction, or placement of electrodes on the distal end 144 of the tip assembly 140.

According to an embodiment of the present invention, the tip assembly 140 may be made from an elastomeric or polymeric thermodynamic bio-compatible material, such as PEBAX, that is bonded onto the distal end 112 of the flexible shaft 110, which may also be made from an elastomeric or polymeric thermodynamic bio-compatible material. Examples of materials that may be used to form the flexible shaft 110 and the tip assembly 140 are well known in the art, and are described, for example, in commonly assigned U.S. Pat. Nos. 5,383,852, 5,462,527, and 5,611,777, which are hereby incorporated by reference in their entirety.

According to one embodiment of the present invention the flexible shaft 110 may be made from a material that is stiffer than the material used to form the proximal end 142 of the tip assembly 140, and the tip assembly 140 may be formed from a variety of bio-compatible materials that have different degrees of stiffness. For example, in one embodiment, the flexible shaft 110 is made from a material having a hardness of approximately 60 Shore D, the proximal end 142 of the tip assembly is made from a material having a hardness of approximately 45-50 Shore D, and the arcuately curved distal end 144 is made from a material having a hardness of approximately 40 Shore D. The increased stiffness of the shaft 110 permits pressure applied to the handle 120 to be more directly translated to the tip assembly 140. Further, the intermediate stiffness of the proximal end 142 of the tip assembly 140 permits movement (i.e., steering) of the tip assembly 140 (described further below) while ensuring that pressure applied to the handle 120 is translated via the shaft 110 to the distal end 144 of the tip assembly 140 to urge the distal end 144 of the tip assembly 140 tight against an endocardial site. Such enhanced contact is advantageous in both mapping and ablation procedures. Further, the relative flexibility of the material from which the distal end 144 of the tip assembly 140 is formed permits the diameter of the arcuately curved distal end 144 of the tip assembly 140 to be changed (increased, decreased, or both) via manipulation of one of the actuators 122, 124 on the handle 120. In another embodiment, the flexible shaft 110 is made from a material having the same degree of hardness as the proximal end 142 of the tip assembly, for example, 45050 Shore D, but the flexible shaft 110 has a larger diameter, and is thus stiffer than the proximal end 142.

To further enhance contact with the endocardial site, the proximal end 142 of the tip assembly 140 may be stiffened, for example with an outer stiffening tube (not shown), just ahead (i.e., proximally) of the approximately ninety degree bend 148. For example, where the tip assembly 140 includes a fixed bend of approximately ninety degrees, the material forming the approximately ninety degree bend 148 may be sufficiently stiffer than that from which the distal end 144 is formed, to further enhance contact with an endocardial or epicardial site.

Although embodiments of the present invention are not limited to any particular length, in one embodiment of the present invention, the length of the flexible shaft is approximately one meter, the length of the proximal end 140 of the tip assembly is approximately 4.5 cm, the length of the distal end 144 of the tip assembly is approximately 6.5 cm, and the length of the approximately ninety degree bend portion is approximately 0.7 cm. It should of course be appreciated that lengths of the different portions of the catheter may be varied, dependent upon the endocardial or epicardial site of interest.

As shown in FIG. 3, the tip assembly 140 may be movable (i.e., steerable) in one or more directions perpendicular to the longitudinal axis of the shaft 110. For example, as illustrated in the embodiment of FIG. 3, the tip assembly 140 is capable of movement in two opposite directions (shown as the Z axis) relative to the longitudinal axis of the shaft via manipulation of one of the actuators 122, 124 on the handle 120 (FIG. 1). In other embodiments, the tip assembly may be moved in only a single direction (e.g., in the positive Z direction), or in a number of different directions (e.g., in the positive and negative Z directions, and the positive and negative Y directions).

As also shown in FIG. 3, and according to one aspect of the present invention, the radius (or alternatively, the diameter) of curvature of the arcuately curved distal end 144 of the tip assembly 140 may be changed from a first diameter D1 to a second diameter D2. Preferably, the radius of curvature of the arcuately curved distal end 144 of the tip assembly 140 may be increased and decreased via manipulation of one of the actuators 122, 124 disposed on the handle 120. This ability to both increase and decrease the radius of curvature of the distal end 144 of the tip assembly 140 permits a single tip assembly 140 to be used in a wide variety of applications and with a wide variety of patients (from adults or large animals to children or small animals),
as it can be adjusted to different diameters to suit the requirements of the patient and the particular medical procedure. It also permits a radially outward force, or alternatively, a radially inward force, to be applied to an endocardial or epicardial site.

According to one embodiment of the present invention, the diameter of the arcuately curved distal end of the tip assembly is approximately 20 mm in a resting state (corresponding to a neutral position of the actuator 122, 124 that controls the radius of curvature of the distal end 144 of the tip assembly 140), but may be decreased to a diameter of approximately 5 mm and increased to a diameter of approximately 50 mm via manipulation of one of the actuators 122, 124. According to this embodiment, the diameter of approximately 20 mm corresponds to an approximately closed circle shown in FIGS. 2 and 3. The diameter of approximately 50 mm corresponds approximately to a semicircle, shown in phantom in FIG. 3, and the diameter of approximately 5 mm corresponds to more than one complete circle (i.e., a spiraling of the distal end) as shown in FIG. 4. Although the present invention is not limited to any particular diameter for the distal end 144 of the tip assembly 140, these dimensions permit the catheter 100 to be well suited for use in mapping and/or ablation procedures relating to blood vessels where focal triggers may be present, such as a pulmonary vein. For example, a diameter of approximately 5 to 50 mm permits the tip assembly to be used for mapping and/or ablation procedures relating to the ostium of a pulmonary vein where focal triggers for cardiac arrythmias may frequently be encountered. These dimensions also permit a single tip assembly 140 to be used in either large or small humans or animals, and for a wide variety of different procedures. It should be appreciated that the above-described dimensions for the diameter of the arcuately curved distal end of the tip assembly correspond to a radius of curvature that is one half that of the indicated diameter (i.e., a diameter of 50 mm corresponds to a radius of curvature of 25 mm, etc.).

Although the radius of curvature of the distal end 144 of the tip assembly 140 described with respect to FIG. 3 is preferably capable of being increased or decreased, the present invention is not so limited. For example, in certain embodiments, the radius of curvature may be changed in only first direction (e.g., increased), while in other embodiments, the radius of curvature may only be changed in a second direction (e.g., decreased). However, in each of the above described embodiments, the distal end 144 of the tip assembly 140 is preferably permanently biased into an arcuate shape in its resting state so that the increase and/or decrease in the radius of curvature is achieved in a known and controlled manner.

Steering and Control of the Tip Assembly

Figure 11:
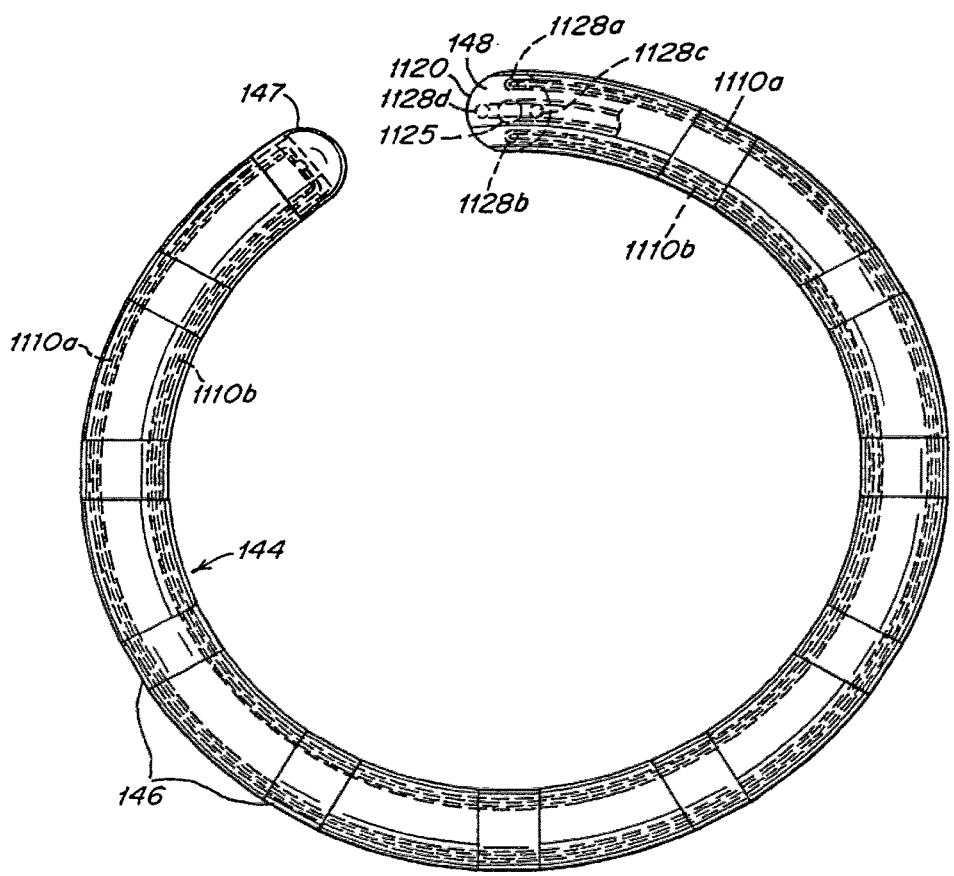
FIG. 11 is an enlarged end elevational view of the distal end tip assembly of FIG. 2.

FIG. 11 is an enlarged end elevational view of the distal end tip assembly 140 of FIG. 2. As shown in FIG. 11, in one embodiment of the present invention, the distal end 144 of the tip assembly 140 includes a pair of cables 110a, 1110b that may be used to change the radius (or alternatively, the diameter) of curvature of the distal end 144 of the tip assembly from a first diameter to a second diameter. In the embodiment illustrated in FIG. 11, the tip assembly includes a core 1120 that includes a plurality of lumens, including a central lumen 1125, and four coaxial lumens 1128a-d disposed about the central lumen 1125. The central lumen 1125 is used to hold one or more electrically conductive wires (not shown in FIG. 11) that are attached to respective electrodes 146, 147 disposed along the distal end 144 of the tip assembly 140. The four coaxial lumens 1128a-d may be used to hold cables that control the orientation of the tip assembly 140 relative to the shaft 110, and that control the radius of curvature of the distal end 144 of the tip assembly 140. As illustrated in FIG. 11, two cables 110a and 110b extend along the length of the distal end 144 of the tip assembly 140, while the two other cables (not shown) terminate prior to the distal end 144. In the embodiment depicted in FIG. 11, the ends of the two cables 110a and 1110b are tied together and potted with an epoxy adjacent the most distal end of the tip assembly 140. In this embodiment, the cables 1110a and 110b are used to control the radius of curvature of the distal end 144 of the tip assembly 140.

Although the tip assembly is described as including a core 1120 that includes a plurality of lumens 1125 and 1128a-d, it should be appreciated that the tip assembly may be constructed in other ways. For example, U.S. Pat. Nos. 5,383,852, 5,462,527, and 5,611,777 describe alternative constructions for the distal end of a catheter, some of which include a central lumen that holds both the electrode wires and the pull cables.

This alternative construction of the distal end tip assembly may also be used with embodiments of the present invention, as the present invention is not limited to any particular construction.

Figure 12:
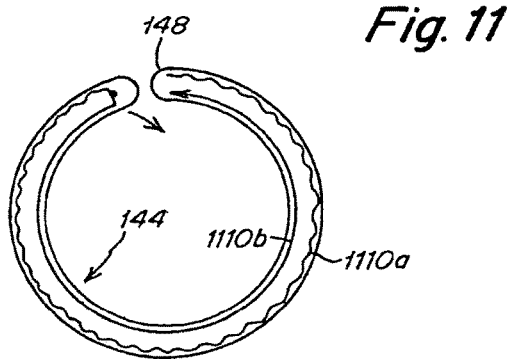
FIG. 12 is a schematic view of the distal end tip assembly of FIG. 11 in a tightly coiled position.
Figure 13:
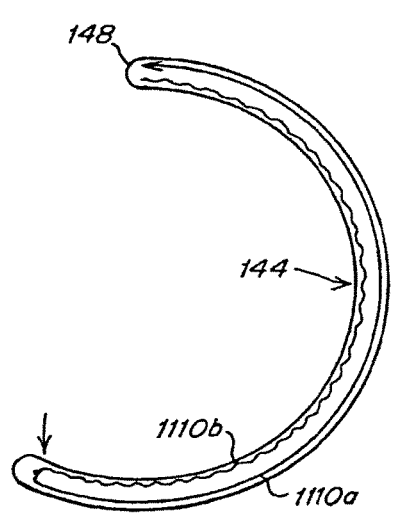
FIG. 13 is a schematic view of the distal end tip assembly of FIG. 11 in a loosely coiled position.

FIGS. 12 and 13 illustrate how the radius of curvature of the distal end 144 of the tip assembly 140 may be changed via manipulation of the cables 1110a, 1110b that are attached to one or more of the actuators 122, 124 on the handle 120 (FIG. 1). In the embodiment illustrated, cables 1110a and 1110d are pull cables that may be formed, for example, from stainless steel wire or any other suitable material. Where the catheter 100 is to be used in an environment where large magnetic fields may be present, for example, in an MRI chamber, each of the cables (and indeed, the electrodes 146, 147) may be made from non-ferromagnetic materials. For example, the electrodes may be made from electrically conductive non-ferromagnetic materials such as platinum, silver, or gold, while the cables may be made from composite materials, such as carbon fiber, or KEVLAR™, or a multiplicity of ultra-high molecular weight polyethelene filaments. It should be appreciated that the cables 1110a and 1110b may alternatively be used as push cables, although the use of push cables generally requires a more rigid and oftentimes larger diameter cable than that required for a pull cable, which is operative under tension, rather than compression. As an example, the diameter of the pull cables may be in the range of 0.003 to 0.004 inches.

As shown in FIGS. 12 and 13, tension applied to cable 1110b results in a decrease in the diameter of curvature of the distal end 144 of the tip assembly 140 (and a corresponding slack in the cable 1110a), while tension applied to cable 110a results in an increase in the diameter of curvature of the distal end 144 of the tip assembly 140.

FIG. 14 is a side elevational view of the distal end of a finished catheter 100 prior to shaping with any one of the jigs described with respect to FIGS. 5-10 below. According to one embodiment of the present invention, the tip assembly 140 may be formed from several different sections that are bonded together and to the shaft 110. The formation of the tip assembly in sections permits greater control of the diameter and stiffness of various sections. As illustrated in FIG. 14, these sections may include a proximal section 1420 that is bonded to the flexible shaft 110, an intermediate section 1480 which may be shaped to bend approximately ninety degrees relative to the shaft 110 and which is bonded to the proximal section 1420, and a distal section 1440 that is bonded to the intermediate section 1480 and which includes a plurality of electrodes and a distal end tip or cap electrode 147.

FIG. 15 is a cross sectional view of the distal end tip assembly 140 of FIG. 14 taken along line 15-15 in FIG. 14. According to one embodiment of the present invention, the tip assembly 140 comprises a tubular proximal section 1420 and a tubular distal section 1440 aligned coaxially with the shaft 110. Between the proximal section 1420 and the distal section 1440 is an intermediate section 1480 that may be shaped to bend approximately ninety degrees relative to the shaft 110. As illustrated, in one embodiment, the proximal section 1420 may be of approximately the same outer diameter as the shaft 110, and the distal section 144 and the intermediate section 1480 can also be of approximately the same outer diameter, but a slightly smaller diameter than the proximal section 1420 and the shaft 110. In other embodiments, the various sections forming the tip assembly 140 may be of the same outer diameter as the shaft 110.

In the illustrated embodiment, the distal section 1440 of the tip assembly 140 terminates in a distal end or cap electrode 147 which is also coaxially aligned with the shaft 110 and sections 1420, 1440, and 1480. A threaded collar 1520 is secured to the distal end of distal section 1440 to retain the electrode cap 147. It should be appreciated that other embodiments need not include the threaded collar 1520 and the distal end or cap electrode 147, and may for example, instead utilize a non-conductive cap.

Shaft 110 may include a single lumen 1525 which extends the length of the shaft 110 from the distal end of the handle 120. The single-lumen 1525 may be used to house the pull cables 1128a-d and the electrode wires 1510. Each pull cable and each electrode wire preferably includes a sheath.

The electrical portion of the tip assembly 140 may include a plurality spaced ring-type electrodes 146 along with a distal end or cap electrode 147. The electrodes provide signal information on heart potentials to the remote recording device 160 (FIG. 1) used by the electrophysiologist. The ring-type electrodes 146 and the cap electrode 147 are electrically connected to respective signal wires 1510. The signal wires 1510 are routed through the length of the core 1120 through a central lumen 1125 in each of the proximal 1420, intermediate 1480, and distal 1440 sections, as illustrated in FIGS. 15, 16, and 17 and attached to a respective electrode 146, 147. The signal wires 1510 are preferably electrically insulated from each other and therefore may all share a single lumen as shown. The signal wires 1510 extend proximally through the handle 120 to the connector 130 which enables the electrodes 146 and 147 to be easily coupled electrically to the recording device 160. In the illustrated embodiment, the two pull cables 1110a and 1110b that extend nearly the length of the tip assembly 140 are used to control the radius of curvature of the distal section 1440. The other two pull cables 1110c and 11110d are used to control bending of the tip assembly 140 in a plane that is perpendicular to the longitudinal axis (L) of the shaft 110 (See FIG. 14). As shown in FIGS. 15, 16, and 17, the pull cables 1110c and 1110d terminate proximally of the intermediate section 1480. In one embodiment, each of the pull cables 1110c and 11110d terminates in a ball 1530 which may be made from any suitable material, and which is larger in diameter than the lumens 1128c and 1128d in which the pull cables are housed. For example, each of the pull cables 1110c and 1110d may be passed through a hole in the ball (not shown) and the end tied to prevent the cable from coming loose. Other methods of terminating the cables 1110c and 1110d are described in the aforementioned patents, for example, by tying the ends of the cables 128c and 1128d together at a distal end of proximal section 1420.

It should be appreciated that an additional pair of pull cables may also be provided to control bending of the tip assembly 140 in a plane that is perpendicular to the longitudinal axis of the shaft 110 and perpendicular to the other plane of motion provided by pull cables 1110c and 1110d. Thus, depending upon the number of pull cables and the number of actuators disposed on the handle 120, the radius of curvature of the distal end of the tip assembly 140 may be increased or decreased, and the orientation of the tip assembly 140 may be changed in two different directions in each of two orthogonal planes (e.g., a Y plane and a Z plane) that are perpendicular to the longitudinal axis of the shaft.

The proximal section 1420 includes a central lumen 1125 for passing all of the electrode wires 1510 to the intermediate 1480 and distal 1440 sections, and for passing two of the pull cables 110a and 110b. The proximal section 1440 also includes two proximal cable lumens 1128c and 1128d which pass pull cables 1110c and 1110d from the lumen 1525 in the shaft 110 through the length of the proximal section 1420. Proximal cable lumens 1128c and 1128d may contain respective stiffening wires 1710 (FIG. 17) to reduce axial twisting of proximal section 1420. The proximal section 1420 includes a reduced diameter proximal end so that the proximal section 144 may be mated to the distal end of the shaft, within the distal end of the shaft 110.

The intermediate section 1480 is thermally bonded to the distal end of the proximal section 1420 and the proximal end of the distal section 1440. The intermediate section 1480 includes two reduced diameter ends so that it may snugly nest inside the proximal and distal sections. The intermediate section 1480 includes two cable lumens 1128a and 1128b and a central lumen 1125. Additional lumens may also be included, as described further below. Pull cables 1110a and 1110b from the central proximal section lumen 1125 are routed to the outwardly disposed cable lumens 1128a and 1128b, respectively, at a point just past the distal end of the central lumen 1125 of the proximal section 1420. A small transition space is provided between the lumens of the intermediate and proximal sections to permit the pull cables 1110a, 1110b to be radially displaced.

The distal section 1440 is thermally bonded to the distal end of the intermediate section 1480 and has approximately the same outer diameter as the intermediate section 1480. The distal end of the intermediate section 1480 is recessed within the distal section 1440 to provide a smooth transition between the two sections. The distal section 1440 also includes two cable lumens 1128a and 1128b and a central lumen 1125. The distal section 1440 may also include additional lumens (shown in FIG. 16), that may be used, for example, to house a control wire for a sliding electrode, to house an irrigation line, to house a wire for a localization sensor, etc. The ends of the pull cables 1110a and 1110b emanating from the outwardly disposed cable lumens 1128a and 1128b, respectively, may be tied together and/or potted with an epoxy. The electrode wires 1510 from the central lumen 1125 are fed through radial apertures in the core 1120 and soldered or welded (or bonded with a conductive epoxy) onto an undersurface of the ring electrodes 146, as illustrated in FIGS. 15A and 16. The wire for the distal end or cap electrode may be fed through the central lumen 1125 and soldered, welded, or epoxied onto the cap electrode 147.

In the embodiment illustrated in FIG. 15, each of the plurality of ring electrodes 146 are recessed within the outer circumferential surface of the distal section to provide a low profile. However, for certain procedures, such as ablation, it may be preferable to have the outer surface of one or more of the electrodes 1546 protrude above the outer circumferential surface of the distal section, such as illustrated in FIG. 15A, and illustrated in phantom in FIG. 16. It should be appreciated that a variety of different types of electrodes may be used with the tip assembly depicted in FIG. 15, as the present invention is not limited to any particular type, or construction of electrode.

Various configurations can be used to locate and anchor the pull cables within the shaft and the proximal, intermediate and distal sections of the tip assembly. In general, it is preferable to conduct the pull cables as close as possible to the outer circumference of the section controlled by the cables in order to increase the bending moment. For this reason, the controlling cables for both the proximal and distal sections are directed to outer lumens, i.e., lumens 1128c and 1128d and lumens 1128a, 1128b. However, prior to reaching the section that is controlled by the cables, the cables are preferably centrally routed, for example in central lumen 1125, so that manipulation of cables controlling movement of more distal sections of the catheter do not affect the orientation of more proximal sections of the catheter. The illustrated construction has been found to be an optimal arrangement from the points of view of manufacturing ease and function. Other arrangements, however, can also be used. For example, the pull cables can be conducted through the proximal, intermediate, and distal sections exclusively through outer lumens. Examples of other arrangements for the pull cables within the tip assembly 140 are described in the aforementioned U.S. Pat. Nos. 5,383,852, 5,462,527, and 5,611,777.

Active Bend

As noted above, the approximately ninety degree bend in the distal end tip assembly 140 may be either fixed (e.g., permanently formed with the use of a jig, such as jigs 500, 700, and 900, described in detail with respect to FIG. 5-10 below), or active (e.g., movable between approximately zero and approximately ninety degrees relative to the longitudinal axis of the shaft 110 of the catheter 100) through the use of an actuator 122, 124 disposed on the handle 120. FIGS. 21 and 21A illustrate an embodiment of the present invention that includes such an "active bend."

As shown in FIG. 21, in one embodiment, the distal end tip assembly 140 includes a proximal section 2120, an intermediate section 2180 that may be actively bent via manipulation of a control cable (FIG. 21A) attached to an actuator (e.g., actuator 122) on the control handle 120 to be approximately perpendicular to the longitudinal axis of the shaft 110, and a distal section 2140 having a radius of curvature that can be adjusted via manipulation of a control cable attached to an actuator (e.g., actuator 124) on the handle 120. The distal section 2140 includes one or more electrodes 146, 147 disposed along a length of the distal section 2140.

As shown in FIG. 21A, which is a cross section of the proximal section 2120 of the tip assembly 140 taken along line 21A-21A in FIG. 21, the cables 1110c and 1110d that control bending of the intermediate section 2180 may be formed from a single cable that is wrapped around a reduced diameter end of the proximal section 2120 and that is recessed within the intermediate section 2128 in a manner similar to that described with respect to FIG. 12 in U.S. Pat. No. 5,383,852. In general, the cable will be wrapped about that portion of the tip assembly that is immediately prior to the point at which bending is to occur. In this embodiment, tension applied to cable 1110c results a bending of the distal section 2140 of the tip assembly 140 in a downward direction (as seen in FIG. 21) to orient the arcuately curved distal section 2140 in a plane that is perpendicular to the longitudinal axis of the shaft 110, and tension applied to cable 1110d results in the bending of the distal section 2140 of the tip assembly 140 in an upward direction (as seen in FIG. 21) to return to its position along the longitudinal axis of the shaft. Because the handle 120 may be rotated one hundred and eighty degrees, the ability to bend the distal section in an opposite direction is unnecessary, but may be provided, if desired. It should be appreciated that in other embodiments, only a single control wire may be used.

To accommodate such an active curve, the material from which the intermediate section 2180 is formed should be less stiff than the material from which the shaft 110 is formed so that bending occurs in the intermediate section 2180. Preferably, the material from which the distal section is formed is less stiff than that from which the intermediate section is formed to permit the radius of curvature of the distal section 2140 to be changed without altering the orientation of the intermediate and proximal sections 2180 and 2120, respectively.

To facilitate bending in a known and controlled manner, the intermediate section 2180 is preferably permanently biased to have a bend of a few degrees relative to the longitudinal axis (L) of the shaft 110. Because the intermediate section 2180 is permanently biased a few degrees away from the longitudinal axis (L) of the shaft 110, tension applied to cable 1110c, for example, results in bending of the intermediate section 2180 in the plane of the bend toward a ninety degree angle with the longitudinal axis (L) of the shaft 110. Tension applied to the opposing cable, for example 1110d, results in bending of the intermediate section 2180 in the plane of the bend back toward the longitudinal axis (L) of the shaft 110. Because the intermediate section 2180 is biased a few degrees away from the longitudinal axis (L) of the shaft 110 in a particular direction, any bending of the intermediate section 2180 occurs in the plane aligned in the same direction as that bend in a known and controlled manner. Were the intermediate section 2180 not biased in a particular direction, bending could occur in any direction.

Electrode Configurations

As noted above, embodiments of the present invention are not limited to a particular construction, type, or number of electrodes disposed along the distal end of the tip assembly. For example, embodiments of the present invention may include a plurality of low-profile ring type electrodes 146 disposed along the distal end of the tip assembly 140, such as shown in FIG. 2, with or without a distal end or cap electrode 147. Alternatively, a plurality of raised profile ring type electrodes may be used, such as the electrode 1546 illustrated in FIG. 15A, with or without a distal end or cap electrode 147. Alternatively still, a combination of raised and low profile electrodes may be used.

Where multiple mapping electrodes are used, pairs of mapping electrodes 146 (FIG. 2) may be used to determine a location of lowest conductivity on the septal wall, or a preferred location to puncture the septal wall during a transeptal procedure. Each of the mapping electrodes 146 may detect a voltage signal, which is transmitted to controller 150 via cable 115 (FIG. 1). Voltage may be measured instantaneously or continuously by each of the electrodes 146. Continuous voltage measurements generate an electrogram (a voltage signal that changes with time) for each electrode. The voltage detected by each electrode may be determined with respect to a reference electrode, termed a unipolar voltage measurement, or may be determined with respect to another electrode of a pair, termed a bipolar voltage measurement. Thus, a pair of mapping electrodes may generate two unipolar electrograms, each with respect to a reference electrode located elsewhere on the catheter 100, or a single bipolar electrogram representing the voltage between each pair of electrodes. As unipolar and bipolar voltage measurement are well understood by those skilled in the art, further discussion is omitted herein.

It should be appreciated that the electrodes may be constructed from a variety of materials, including non ferromagnetic materials such as gold, platinum, and silver, or they may be constructed from a conductive epoxy. The electrodes may be individual electrodes, or may be continuous electrodes, similar in construction to a coiled spring wrapped about the distal end of the tip assembly. The electrodes may be fixed in position along the distal end of the tip assembly, or alternatively, may be movable along a length of the distal end of the tip assembly. An example of such a movable electrode is now described with respect to FIG. 18.

As shown in FIG. 18, the distal end 144 of the tip assembly 140 may include a movable electrode 1846 that is movable between a first position and a second position spaced apart along a length of the distal end 144 of the tip assembly 140. In the embodiment illustrated, the movable electrode 1846 slides along a length of the distal end 144 than spans approximately 360 degrees, and when used for ablation, may be used to form a circular lesion. The very distal end of the tip assembly may include a cap electrode 1847, or alternatively, the cap may be made from a non-conductive material and may simply serve to terminate the very distal end of the tip assembly. Where a cap electrode 1847 is used, an insulating spacer may be placed proximally of the cap electrode to prevent the movable electrode 1846 from electrically contacting the cap electrode 1847.

As shown in FIG. 19, which is a cross sectional side view of the distal end of the tip assembly in FIG. 18 taken along line 19-19, the electrode 1846 may be attached to a cylindrically-shaped plastic slider 1910 that that can slide back and forth along a length of the distal end 144 of the tip assembly. In the embodiment shown, the distal end of a metal push/pull wire 1920 is welded to an outer surface of the electrode 1846, with the proximal end of the push/pull 1920 wire being attached to an actuator 122, 124 on the handle 120. The push/pull wire 1920 may be disposed within the central lumen 1125 from the handle 120 to the intermediate section 1480 of the tip assembly 140 (FIG. 15), wherein it then passes through one of the outer lumens 1110c, 1110d of the distal section. The distal end of the push/pull wire 1920 emanates through a slit 1930 in the core 1120. It should be appreciated that in embodiments where it is desired that the push/pull wire 1920 not be electrically connected to the electrode, the push/pull wire 1920 may be attached to the plastic slider 1910, rather than to the electrode 1846. It should also be appreciated that the push/pull wire 1920 need not be made from metal, as non-conducting materials may also be used, as known to those skilled in the art.

FIG. 20 is a cross sectional end view of distal end of the tip assembly illustrated in FIG. 19, taken along line 20-20. FIG. 20 illustrates the slit 1930 in the core 1120 through which the push/pull wire 1920 protrudes, with the remaining elements having already been described. Further details of the sliding electrode described with respect to FIGS. 18-20 are provided in commonly assigned U.S. Pat. No. 6,245,066, which is hereby incorporated by reference in its entirety.

The Handle

A handle assembly in accordance with one embodiment of the invention, is shown in FIGS. 22-33. The handle configuration shown in these drawings uses rotational movement of the thumbwheel actuator 122 to selectively control the tension applied to the pull cables 1110c and 1110d which control the orientation of the tip assembly 140 relative to the longitudinal axis of the shaft 110, and linear movement of the slide actuator 124 to selectively control the tension applied to pull cables 1110a and 1110b that control the radius of curvature of the distal end 144 of the tip assembly 140.

Figure 22:
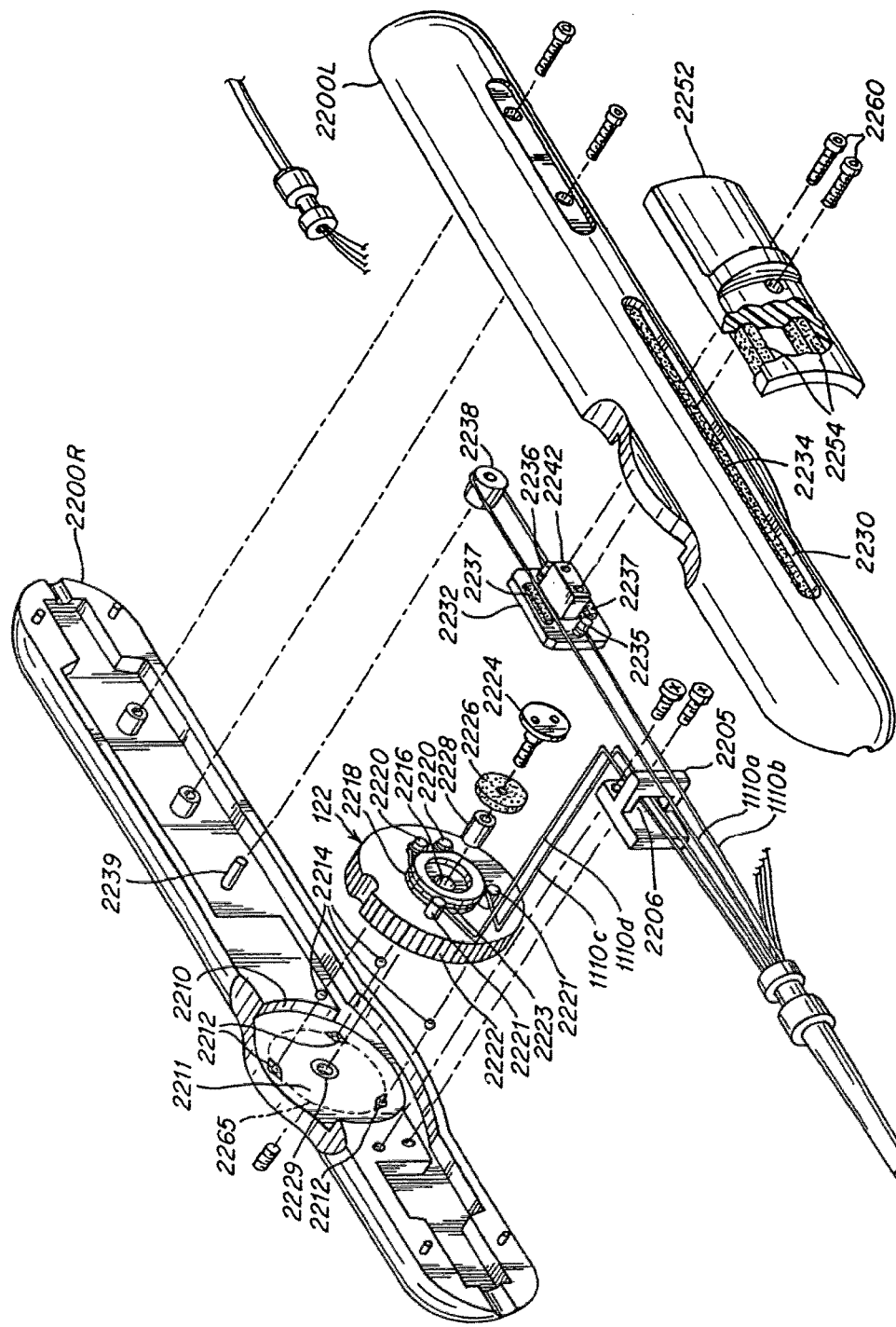
FIG. 22 is an exploded view of a handle, taken along line 22-22 in FIG. 1, that may be used with the catheter system of FIG. 1 according to another embodiment of the present invention.

Referring to FIG. 22, the handle 120 comprises a housing having a left section 2200L and a right section 2200R. These two sections 2200L and 2200R are somewhat semicircular in cross section and have flat connecting surfaces which may be secured to each other along a common plane to form a complete housing for the handle 120. The outer surfaces of the handle 120 are contoured to be comfortably held by the user.

A wheel cavity 2210 is formed within the right section 2200R of the handle 120. The wheel cavity 2210 includes a planar rear surface 2211 which is generally parallel to the flat connecting surface of the handle 120. The thumb wheel actuator 122 is a generally circular disc having a central bore 2216, an integrally formed pulley 2218, and upper and lower cable anchors 2220. Upper and lower cable guides 2221 serve to retain the cables 1110c and 1110d within a guide slot or groove 2223 formed in a surface of the integrally formed pulley 2218. In the embodiment illustrated, the thumbwheel 122 rotates about a sleeve 2228 inserted in the central bore 2216. The thumbwheel 122 is held in position by a shoulder nut 2224 that mates with a threaded insert 2229 in the planar rear surface 2211 of the right section 2200R of the handle 120. To provide friction that permits the thumbwheel to maintain its position even when tension is applied to one of the cables 1110c, 1110d, a friction disk 2226 is provided between the shoulder nut 2224 and the thumbwheel 122. Tightening of the shoulder nut 2224 increases the amount of friction applied to the thumbwheel 122.

A peripheral edge surface 2222 of the thumb wheel 122 protrudes from a wheel access opening so that the thumb wheel 122 may be rotated by the thumb of the operator's hand which is used to grip the handle 120. To ensure a positive grip between the thumb wheel 122 and the user's thumb, the peripheral edge surface 2222 of the thumb wheel 122 is preferably serrated, or otherwise roughened. Different serrations on opposite halves of thumb wheel 122 enable the user to "feel" the position of the thumb wheel.

The left section 2200L supports part of the mechanism for selectively tensioning each of the two pull cables 1110a and 110b that control the radius of curvature of the distal end 144 of the tip assembly 140. To accommodate the protruding portion of the thumb wheel 122, the left handle section 2200L includes a wheel access opening similar in shape to the wheel access opening of the right handle section 2200R. It also includes an elongated slot 2230 in its side surface.

A slider 2232 is provided with a neck portion 2242 which fits snugly within the slot 2230. The slider 2232 includes a forward cable anchor 2235 and a rear cable anchor 2236 for anchoring the pull cables 1110a and 1110b. Pull cable 1110b is directly attached to the forward cable anchor 2235 and becomes taught when the slider 2232 is moved toward the distal end of the handle 120. Pull cable 1110a is guided by a return pulley 2238 prior to being attached to the rear cable anchor 2236 and becomes taught when the slider 2232 is moved toward the proximal end of the handle 120. The return pulley 2238 is rotatably attached to a pulley axle 2239 which is supported in a bore (not shown) in the flat surface of the right handle section 2200R. The return pulley 2238 may include a groove (not shown) to guide pull cable 1110a. In the illustrated embodiment, a cable guide 2205 is attached to the right handle section 2200R to guide the cables 1110a-1110d and prevent their entanglement with one another. As shown, cables 110a and 1110b are routed up and over the cable guide 2205, while cables 1110c and 1110d are routed through a gap 2206 in the cable guide 2205. Grooves may be formed in a top surface of the cable guide 2205 to keep cables 1110a and 1110b in position, although they could alternatively be routed through holes formed in the cable guide 2205, or by other suitable means.

A slider grip 2252 is attached to the neck portion 2242 of the slider 2232 and positioned externally of the handle 120. The slider grip 2252 is preferably ergonomically shaped to be comfortably controlled by the user. Together, the slider 2232 and the slider grip 2252 form the slide actuator 124 depicted in FIG. 1. Preload pads 2254 are positioned between the outer surface of the left handle section 2200L and the slider grip 2252 (shown in FIGS. 22 and 25). By tightening the screws 2260 that attach the slider grip 2252 to the slider 2232, friction is applied to the slider 2232 and thus, to the pull cables 1110a, 1110b. Preload pads 2237 may also be placed on a surface of the slider 2232 for a similar purpose.

A dust seal 2234 (FIGS. 22 and 26) having an elongated slit and preferably made from latex is bonded along the slot 2230 within the left handle section 2200L. The neck portion 2242 of the slider 2232 protrudes through the slit of the dust seal 2234 so that the slit only separates adjacent to the neck portion 2242. Otherwise, the slit remains "closed" and functions as an effective barrier preventing dust, hair and other contaminants from entering the handle 120. Further details of the handle 122 are described in U.S. Pat. Nos. 5,383,852, 5,462,527, and 5,611,777.

According to a further aspect of the present invention, each of the thumbwheel actuator and the slide actuator may include means for imparting a first amount of friction on at least one pull cable to which the actuator is attached when the actuator is in a first position, and for imparting a second and greater amount of friction on the at least one pull cable when the actuator is moved away from the first position. According to this aspect of the present invention, the first position may correspond to a neutral position of the actuator wherein the tip assembly is aligned with the longitudinal axis of the shaft, or a neutral position of the actuator wherein the radius of curvature of the distal end of the tip assembly is neither being actively reduced or increased, and the second position may correspond to a position of the actuator that is other than the neutral or rest position.

As should be appreciated by those skilled in the art, it is desirable that the actuators for changing the orientation of the tip assembly and for controlling the radius of curvature of the distal end of the tip assembly remain in a fixed position, once actuated. Conventionally, this has been achieved by providing a sufficient amount of friction between the actuator and another surface on the handle 122 to resist movement of the actuator unless a certain amount of force is applied to the actuator. For example, in FIG. 22, by tightening shoulder nut 2224 that holds the thumbwheel in position, a greater amount of force must be applied to the thumbwheel to rotate the thumbwheel from one rotational position to another. Similarly, and with respect to the slide actuator 124, by tightening the two screws 2260 that hold the slider grip 2252 in position against an undersurface of the handle section, a greater amount of force must be applied to the slide actuator 124 to move the slide actuator 122 from one position to another.

Although this conventional approach is straightforward, it results in the same amount of friction being applied to the actuator(s) in all positions, and not merely those positions that deviate from a neutral or rest position. Thus, in use, it can be difficult to ascertain whether the orientation of the tip assembly or the radius of curvature of the distal end of the tip assembly is in a neutral state, without visually looking at the handle. This can be problematic, as the user of the catheter would need to divert his or her attention to visually inspect the position of the actuator(s). Further, Applicants have determined that the frictional force imparted by the mechanisms that maintain the cables and actuators in a fixed position can significantly decrease over time, for example, while stacked on the shelf, oftentimes requiring that the mechanisms used to impart such friction (e.g., the shoulder nut and the screws) be tightened prior to use. It is believed that this phenomena is due to material creep associated with the various materials used to form the actuator mechanisms. This decrease in frictional force is especially apparent where the catheter has been brought to elevated temperatures during a sterilization cycle, as the materials from which the handle and the control mechanisms are formed have a tendency to yield at elevated temperatures. Although the various mechanisms may be tightened after sterilization, such tightening may contaminate the sterile nature of the catheter, and is undesirable in a clinical setting.

According to a further aspect of the present invention, each of the thumbwheel actuator and the slide actuator may include means for imparting a first amount of friction on at least one pull cable to which the actuator is attached when the actuator is in a first position, and for imparting a second and greater amount of friction on the at least one pull cable when the actuator is moved away from the first position. This difference in the frictional force can be perceived by the user to alert the user as to when the actuator is in a neutral or rest position, without visually inspecting the actuator. Further, because the frictional forces on the actuating mechanisms are reduced in a neutral or rest position, the catheter may be sterilized with the actuator(s) in a neutral or rest position, thereby reducing yielding of the actuation mechanism during sterilization.

According to one embodiment that is directed to the thumbwheel actuator, the means for imparting different amounts of friction may include a plurality of detents formed in the planar rear surface of the handle housing that cooperate with corresponding plurality of detents in a lower surface of the thumbwheel. In this embodiment, each of the plurality of detents in the lower surface of the thumbwheel receives a ball or bearing that sits partially within the respective detent. In a first neutral position, each of the balls also rest within a respective detent in the rear surface of the handle and exert a first amount of friction on the thumbwheel and the pull cables attached thereto. But, as the thumbwheel is rotated, the balls ride outside the detent in the rear surface of the handle onto the elevated surface above, thereby exerting a second and greater amount of friction on the thumbwheel and the pull cables attached thereto. According to one embodiment, this second amount of friction is sufficient to prevent the thumbwheel from returning to its neutral position. FIGS. 22, 26, 27, and 28 illustrate one implementation of a means for imparting different amounts of friction for a thumbwheel actuator 122 according to this embodiment of the present invention.

Figure 26:
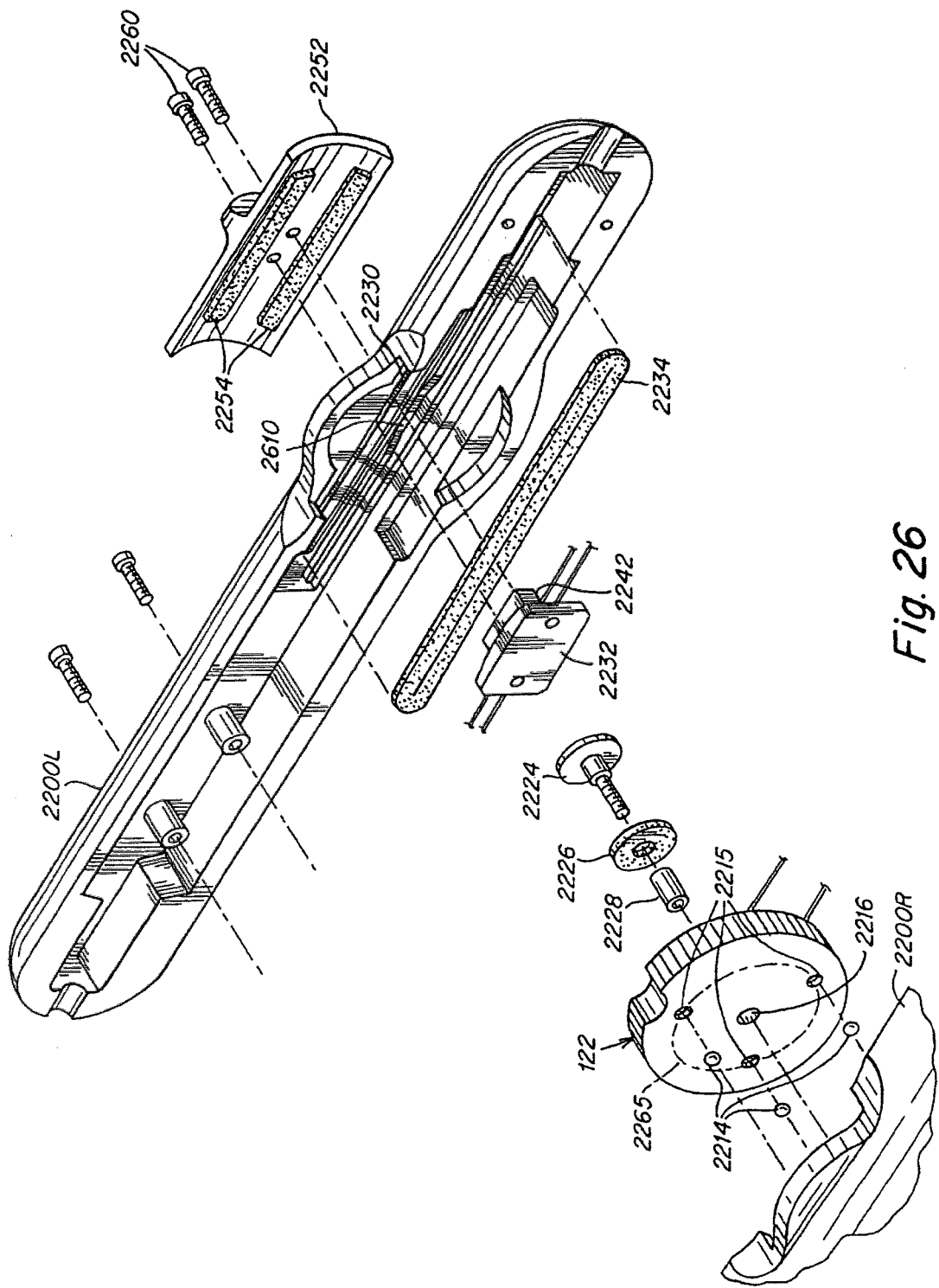
FIG. 26 is an exploded perspective view of the left section of the handle of FIG. 22.
Figure 27:
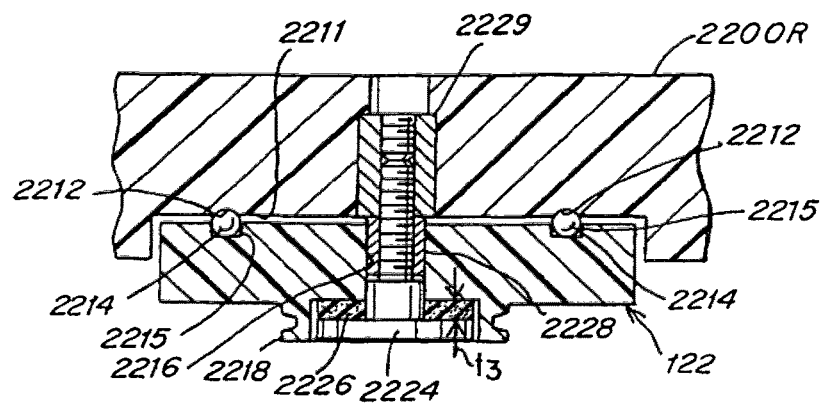
FIG. 27 is a schematic cross sectional view of a thumbwheel actuator for the handle of FIG. 22 in a neutral or unloaded state.
Figure 28:
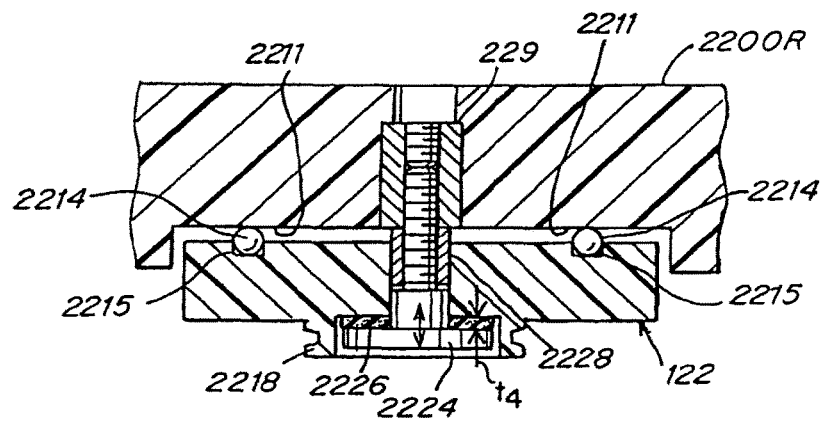
FIG. 28 is a schematic cross sectional view of the thumbwheel actuator for the handle of FIG. 22 in a deployed or loaded state.

As shown in FIGS. 22, 26, 27, and 28, the planar rear surface 2210 of the right section 2200R includes a plurality of detents 2212 formed therein. A corresponding number of detents 2215 are provided in an undersurface of the thumbwheel 122 (FIGS. 26-28). Within each of the plurality of detents 2215 in the undersurface of the thumbwheel is a ball or bearing 2214. The balls or bearing may be made from any suitable material, such as stainless steel, or may alternatively be made from a hard plastic. The balls or bearings 2214 may be fixed in position for example, with an epoxy, or permitted to rotate within the detents 2215. It should be appreciated that the balls or bearings 2214 may alternatively be seated within the detents 2212 in the planar rear surface 2211 of the right section of the handle 2200R. In a neutral or rest position, for example, corresponding to an orientation of the tip assembly that is parallel to the longitudinal axis of the shaft, each of the plurality of balls rests within a corresponding detent 2212 in the planar rear surface 2211. Such a resting or neutral state is depicted in FIG. 27 which is a schematic cross sectional view of the thumbwheel of FIG. 22. As may be appreciated, this neutral or rest position corresponds to a position of reduced friction on the thumbwheel 122 in which the friction disk 2226 is compressed to only a small degree, and thus, to a reduced frictional force on the pull cables that are attached to the thumbwheel.

As the thumbwheel 122 is rotated from this neutral or rest position, the balls 2214 ride up and out of their respective detents 2212 and along the path 2265 indicated in FIG. 22. In this second position wherein each of the balls contacts the elevated planar rear surface 2211, a second and greater amount of friction is imparted to the thumbwheel, and thus, the pull cables attached thereto, that tends to prevent the thumbwheel from moving to another position without further rotational force applied to the thumbwheel. FIG. 28 is a schematic cross sectional view of the thumbwheel of FIG. 22 illustrating a state in which the thumbwheel is in a position other than the neutral or rest position. As can be seen in FIG. 28, each of the balls 2214 rests upon the elevated planar rear surface 2211 and the friction disk 2226 is compressed relative to that shown in FIG. 27. As shown best in FIG. 22, each of the detents 2212 in the planar rear surface 2211 may include lead in/lead out sections 2267 that are gradually tapered to the level of the planar rear surface 2211 to facilitate smooth movement of the balls 2214 out of and into the detents 2212.

Although the present invention is not limited to the number of detents 2212, 2215 incorporated into the handle and the thumbwheel, Applicants have found that three detents spaced equally about a circumference of the planar rear surface 2211 and the thumbwheel 122 distributes stress evenly about the thumbwheel 122 and permits a sufficient amount of rotation before another detent 2212 is encountered. Furthermore, although the present invention is not limited to the amount of force applied to the thumbwheel to change the position of the thumbwheel, Applicants have empirically determined that a force of approximately 4 to 8 pounds is sufficient to resist any forces on the pull cables. Moreover, this amount of force is sufficient so that the thumbwheel cannot be moved inadvertently, and does not require great strength by the user. This amount of force also accounts for any yielding during storage and/or sterilization.

Although this embodiment of the present invention has been described in terms of a plurality of detents in a surface of the handle and a corresponding number of detents that hold a ball or bearing in an undersurface of the thumbwheel, the present invention is not so limited. For example, and as discussed above, the detents in the planar surface 2211 of the handle 120 may hold the balls or bearings 2214 and not the thumbwheel. Moreover, it should be appreciated that other means of imparting different frictional forces on the thumbwheel may be readily envisioned. For example, rather than detents, the rear planar surface 2211 may be contoured to include a plurality of ramps (for example, three ramps). The undersurface of the thumbwheel 122 may include a corresponding plurality of complementary shaped ramps such that when the thumbwheel 122 is in a neutral or rest position, a minimum of friction is imparted, and as the thumbwheel 122 is rotated, the heightened surface of the ramps on the undersurface of the thumbwheel 122 contacts a heightened surface of the ramps in the planar surface. As the thumbwheel 122 is rotated further, addition friction is imparted.

According to another embodiment that is directed to the slide actuator, the means for imparting different amounts of friction may include a ramp disposed on or formed within the handle 120. In this embodiment, the apex of the ramp corresponds to a neutral position of the slide actuator 122. In this neutral position, a minimum amount of friction is applied to the slider 2232 and the pull cables 1110a, 1110b attached thereto. As the slider 2232 is moved forward or backward away from the neutral position, the slider 2232 is pushed toward the thumbwheel and an interior surface of the housing to impart a great amount of friction on the slider and the pull cables attached thereto. As with the thumbwheel, this second amount of friction is sufficient to prevent the slider from returning to its neutral position.

Figure 23:
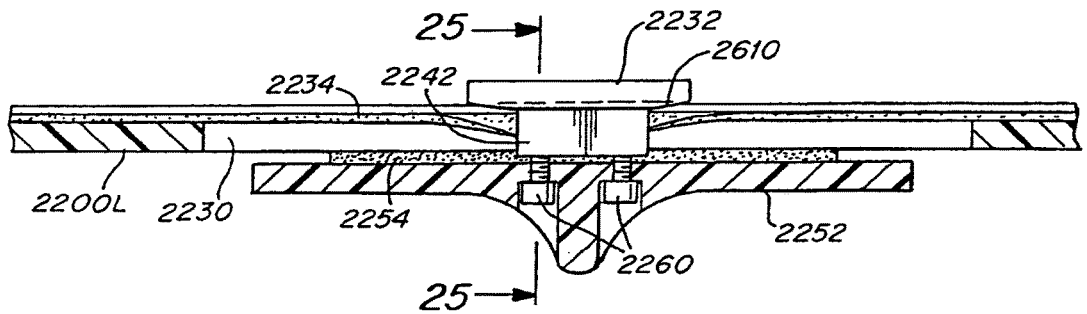
FIG. 23 is a schematic cross sectional view of a slide actuator for the handle of FIG. 22 in a neutral or unloaded state.
Figure 24:
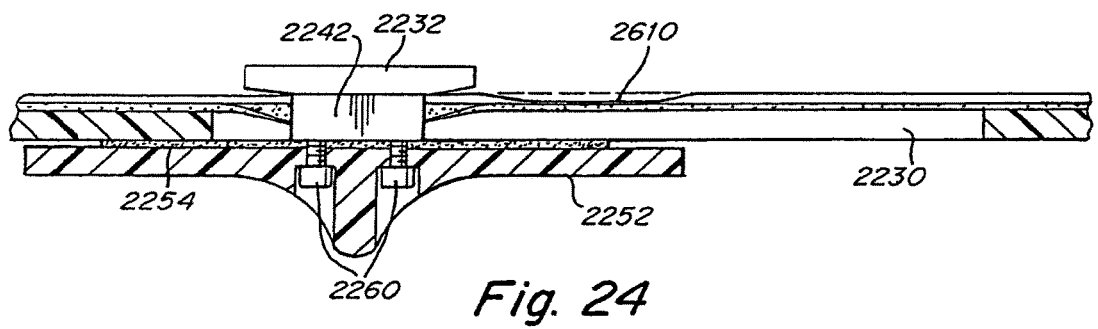
FIG. 24 is a schematic cross sectional view of a slide actuator for the handle of FIG. 22 in a deployed or loaded state.
Figure 25:
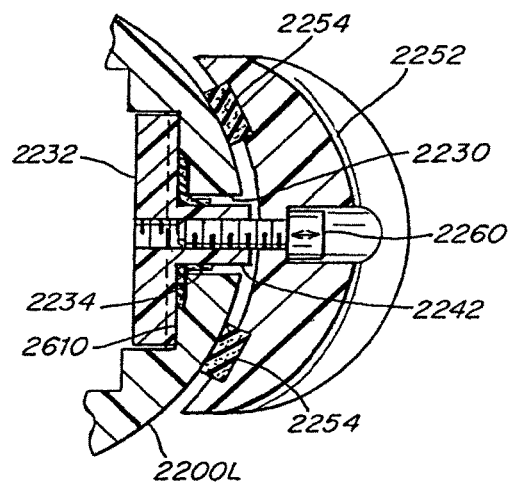
FIG. 25 is a cross sectional end view of the slide actuator of FIG. 23 taken along line 25-25 in FIG. 23.

FIGS. 23, 24, and 26 illustrate one implementation of a means for imparting different amounts of friction for a slide actuator 124. As shown in these Figures, the undersurface of the left section 2200L includes a ramp 2610. The ramp may be integrally formed within the left section 2200L of the handle 120, or alternatively, the ramp 2610 may be separate from the handle and attached thereto. As illustrated in FIG. 26 which is a schematic cross sectional view of the slide actuator 124 shown in FIGS. 1 and 22, the ramp 2610 includes a central section of decreased thickness and proximal and distal sections that increase in thickness away from the central section until flush with the undersurface of the left section. The top surface of the slider 2232 that contacts the undersurface of the left section 2200L of the handle may have a complementary shape to the ramp as shown in FIGS. 23 and 24. In the position shown in FIG. 23, the slide actuator is in a neutral or rest position corresponding to a first radius of curvature of the distal end of the tip assembly. The two screws 2260 force the slider grip 2252 and the slider 2232 closer to one another and compress the preload pads 2254 therebetween. In the neutral or rest position shown in FIGS. 23 and 25, the preload pads 2254 are compressed to only a minimal extent. However, as the slider 2232 is moved away from the neutral or resting position, the shape of the ramp 2610 (and the slider 2332) imparts an additional frictional force that tends to separate the slider 2232 from the slider grip 2252, thereby compressing the preload pads 2254 to a greater extent, as illustrated in FIG. 24. This additional frictional force resists the slide actuator 124 from changing position, absent further force on the slide actuator 124.

Although this embodiment of the present invention has been described in terms of a ramp formed within or disposed on an undersurface of the handle 122, the present invention is not so limited. For example, the ramp may alternatively be formed on an outer surface of the handle and provide similar functionality. Other means for imparting different frictional forces on the slide actuator may be readily envisioned by those skilled in the art.

Although the above described embodiments for imparting a varying amount of friction on at least one pull cable have been described with respect to a catheter in which the diameter of curvature of the distal end, or the orientation of the distal end of the tip assembly, can be changed by manipulation of an actuator attached to the pull cable, the present invention is not so limited. For example, the means for imparting a varying amount of friction may also be used with a push/pull cable and a movable electrode described above. Alternatively, the means for imparting a varying amount of friction may be used to impart varying amounts of friction to a cable that is used to deploy a braided conductive member in the manner described in co-pending and commonly assigned U.S. patent application Ser. No. 09/845,022, entitled APPARATUS AND METHODS FOR MAPPING AND ABLATION IN ELECTROPHYSIOLOGY PROCEDURES, filed Apr. 27, 2001, and incorporated herein by reference. Accordingly, it should be appreciated that this embodiment of the present invention may be used to impart varying amounts of friction on any cable that controls movement of one portion of the catheter with respect to another.

Figure 29A:
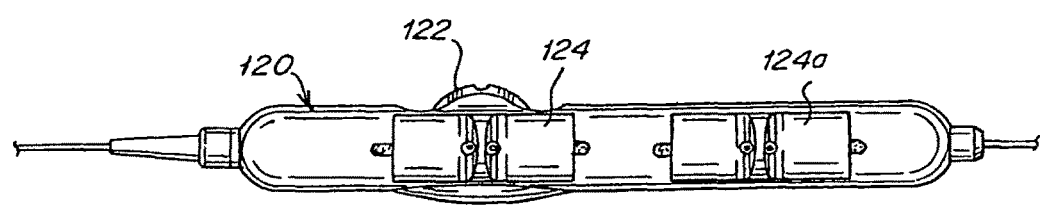
FIG. 29A is an elevational view of another handle that may be used with the catheter system of FIG. 1 according to another embodiment of the invention that includes a third actuator.
Figure 29B:
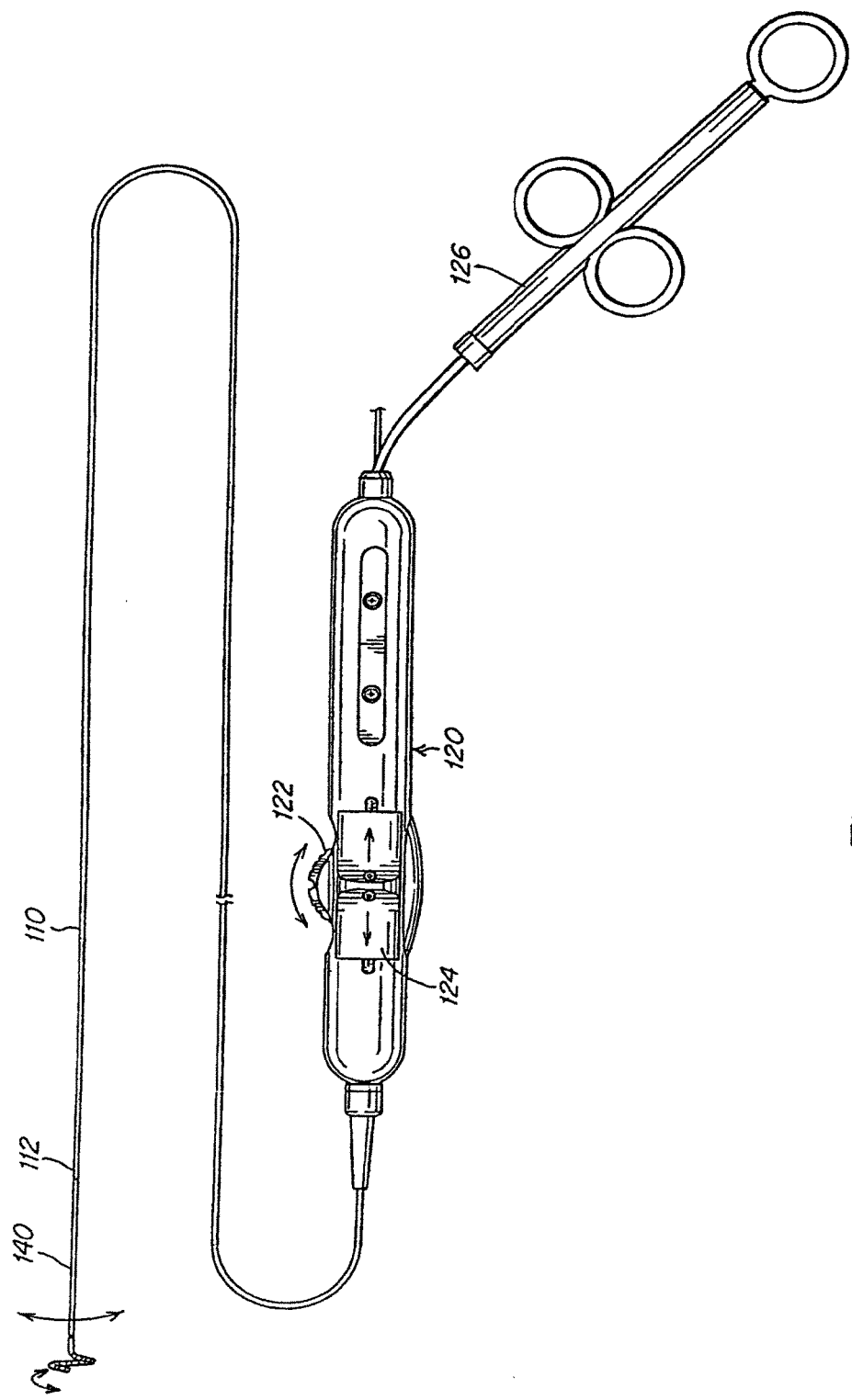
FIG. 29B is a schematic view of another handle according to another embodiment of the invention that includes a plunger-type third actuator.

FIG. 29A illustrates another handle that may be used with embodiments of the present invention. In the embodiment depicted in FIG. 29A, the handle 120 includes three actuators 122, 124, and 124a for controlling movement of the tip assembly 140. For example, the thumbwheel actuator 122 may be used to change the orientation of the tip assembly 140 relative to the longitudinal axis of the shaft 110 of the catheter 100 in one or two different directions depending on the number of cables attached thereto. The first slide actuator 124 may be used to increase and/or decrease the radius of curvature of the distal end 144 of the tip assembly 140. The second slide actuator 124a may be used to control the orientation of the of the tip assembly 140 relative to the longitudinal axis of the shaft 110 of the catheter 100 in one or two different direction of movement that are orthogonal to the directions provided by use of the thumbwheel actuator 122. Alternatively, the second slide actuator 124A may be used to move a sliding electrode (See FIG. 18) proximally and distally along the distal end of the tip assembly. Alternatively still, the thumbwheel actuator 122 or the first slide actuator 124 may be used for changing the orientation of the tip assembly or the radius of curvature of the distal end in a first direction, and the second slide actuator 124a may be used for changing the orientation of the tip assembly or the radius of curvature in the opposite direction. Alternatively still, the first slide actuator 124 may be used for controlling an active bend (see FIG. 21), the thumbwheel actuator 122 may be used for changing the radius of curvature of the distal end of the tip assembly, and the second slide actuator 124a may be used for changing the orientation of the tip assembly in a first and/or second direction (e.g., for steering of the proximal end of the tip assembly.) FIG. 29B illustrates another handle that includes a third actuator. In the embodiment illustrated in FIG. 29B, the third actuator is a plunger-type actuator 126 that is conventionally used for a variety of different purposes in the medical industry. In the illustrated embodiment, the plunger-type actuator may be used to move a sliding electrode proximally and distally along the distal end of the tip assembly, with the thumbwheel 122 and slide 124 actuators being used for steering of the proximal end of the tip assembly and changing the radius of curvature of the distal end of the tip assembly, respectively, or vice versa. Although the use of a handle having up to three different actuators has been described, it should be appreciated that more than three different actuators may be provided. For example, a thumbwheel actuator, two slide actuators, and a plunger-type actuator may be used to control an active bend, a sliding electrode, changing the radius of curvature of the distal end, and steering of the proximal end of the tip assembly.

Figure 30:
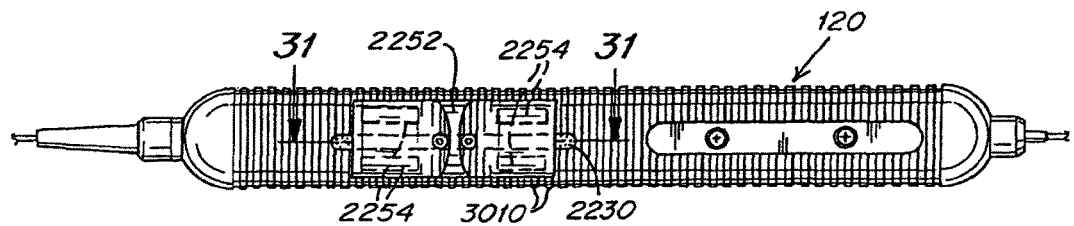
FIG. 30 is a side elevational view of a handle that may be used with the catheter system of FIG. 1 and which includes features that provide tactile feedback to a user when using one of the actuators.
Figure 31:
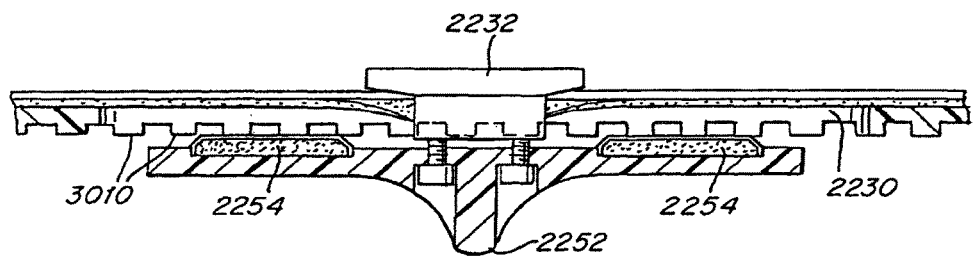
FIG. 31 is a schematic cross sectional view of one implementation for providing tactile feedback to a user that is adapted for use with the slide actuator of FIG. 30.
Figure 32:
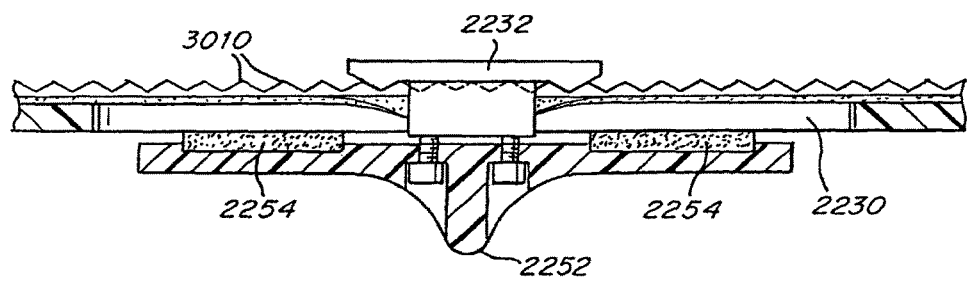
FIG. 32 is a schematic cross sectional view of another implementation for providing tactile feedback to a user that is also adapted for use with the slide actuator of FIG. 30.

FIGS. 30-32 illustrate a control handle for a catheter according to another embodiment of the present invention. As illustrated in FIG. 31, a surface of the handle 120 may include a plurality of ribs or detents 3010 to provide tactile feedback to a user. For example, as the slider grip 2252 is moved proximally and distally on the handle, this movement can be felt by the user. Such feedback permits the user to understand that the radius of curvature of the distal end of the tip assembly, or the orientation of the tip assembly has been changed, without requiring the user to visually perceive the movement of the slider grip 2252. In the embodiment illustrated in FIG. 31, the plurality of ribs are formed integrally with the handle 120 and disposed on an outer surface thereof. To prevent the preload pads 2254 from catching on the ribs or detents 3010, a hard thin layer of material such as plastic may be applied to the surface of the preload pads that contact the outer surface of the handle 120. In the embodiment shown, the leading and trailing edges of the pads 2254 are also curved away from the outer surface of the handle 120 to avoid rough movement.

FIG. 32 illustrates an alternative embodiment of the handle 120 that includes a plurality of ribs or detents 3010 that are formed integrally with the handle 120 and disposed on an inner surface of the handle 120. As the preload pads 2252 do not directly contact the ribs or detents 3010, a hard layer such as that described above with respect to FIG. 31 is not necessary. With each of the embodiments described above, it should be appreciated that the ribs or detents 3010 should be large enough to provide tactile feedback to the user, but not so large as to be disturbing to the user, or to result in rough and abrupt movement of the slide actuator 124 when moved from one position to another. Applicants have empirically determined that a protrusion of the ribs or detents 3010 approximately 1 mm above, or below the surface of the handle meets these objectives. Although the use of ribs or detents has been described with respect to providing feedback to a user on movement of the distal end of the catheter, the present invention is not so limited. For example, the ribs or detents may be used to provide feedback relating to movement of a movable electrode, or a braided conductive mesh.

Accordingly, the use of tactile features for providing feedback to a user may be used wherever it is useful to provide feedback to a user on the movement of one portion of the catheter with respect to another.

According to another embodiment of the present invention, a handle for use with a catheter having an elongated shaft and a tip assembly is provided. According to this embodiment, the handle may include graphical indicia indicative of a radius of curvature of a distal end of the tip assembly. This embodiment is now described with respect to FIG. 33.

Figure 33:
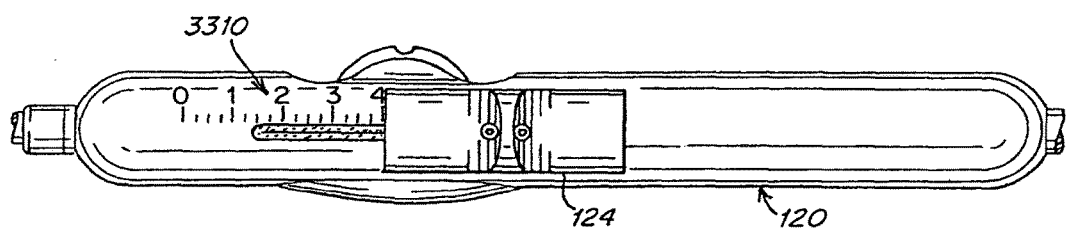
FIG. 33 is a side elevational view of an handle that includes graphical indicia indicative of a radius of curvature of the distal end tip assembly according to another embodiment of the present invention.

As shown in FIG. 33, the handle 120 of the catheter 100 can include graphical indicia 3310 that identifies the radius of curvature of the distal end of the tip assembly.

In the embodiment shown, the graphical indicia 3310 are disposed on the handle 120 adjacent to the slide actuator 124, which in this embodiment controls the radius of curvature of the distal end of the tip assembly. As illustrated, the graphical indicia 3310 identify the diameter of curvature in centimeters, with a position of two centimeters corresponding to a neutral position of the slide actuator. Movement of the slide actuator 124 distally on the handle 120 increases the radius of curvature of the distal end of the tip assembly, and movement of the slider 124 proximally on the handle 120 decreases the radius of curvature. Although not illustrated in FIG. 33, the graphical indicia 3310 may also identify the number of circles formed by the distal end of the tip assembly. For example, a first numeric indicator can precede each of the illustrated numeric indicators to identify the number of circles formed by the distal end of the tip assembly. For example, an indicator of 2.1 can indicate two complete circles of the distal end of the tip assembly with a diameter of 1 cm, with an indicator of 1.2 indicating one complete circle of the distal end of the tip assembly with a diameter of 2 cm. Alternatively, the number of circles formed by the distal end of the tip assembly may be placed on the other side of the slide actuator 124. Other representations of both the diameter of curvature and the number of circles formed by the distal end of the tip assembly may be readily envisioned. It should be appreciated that the graphical indicia permit a user to roughly determine the diameter of an endocardial or epicardial site without recourse to other instrumentation, other than the catheter itself.

Although the provision of graphical indicia has been described with respect to the slide actuator 124, it should be appreciated that a similar provision may be made for the thumbwheel actuator 122. In general, although the provision of graphical indicia may associated with the thumbwheel 122 may not be very useful when related to the orientation of the tip assembly, the operation of the thumbwheel 122 and the slide actuator 124 may be reversed, such that the thumbwheel 122 is used to control the radius of curvature of the distal end of the tip assembly, and the slide actuator 124 is used to control the orientation of the tip assembly. Where the thumbwheel 122 is used to control the radius of curvature of the distal end of the tip assembly, graphical indicia 3010 may be provided on the thumbwheel at different rotational positions (e.g., at zero degrees, at thirty degrees, as sixty degrees, etc. to serve a similar purpose.

Although the provision of graphical indicia has been described with respect to providing feedback to a user on the radius of curvature of the distal end of the catheter, it should be appreciated that other uses may be readily envisioned. For example, the use of graphical indicia may be used to identify the state of deployment of a braided mesh that is disposed at the distal end of the catheter, or to identify the location of a movable electrode that is disposed on the distal end of the catheter.

Temperature Sensing and Localization

Temperature sensing refers to a number of techniques whereby the temperature in the vicinity surrounding distal end 144 of the tip assembly 140 may be measured. Measuring temperature is important, particularly during ablation procedures, so as to avoid overheating or charring tissue. The catheter of the present invention can provide for measuring the temperature of the distal end 144 of the tip assembly 140 and the mapping electrodes disposed thereon at the same time. The temperature of the distal end 144 can then be used to provide feedback for control of ablation energy generator 170 and the temperature of the mapping electrodes can be monitored to be certain that the tissue that is being ablated is in fact being destroyed or rendered non-electrically conductive.

Figures 34, 35:
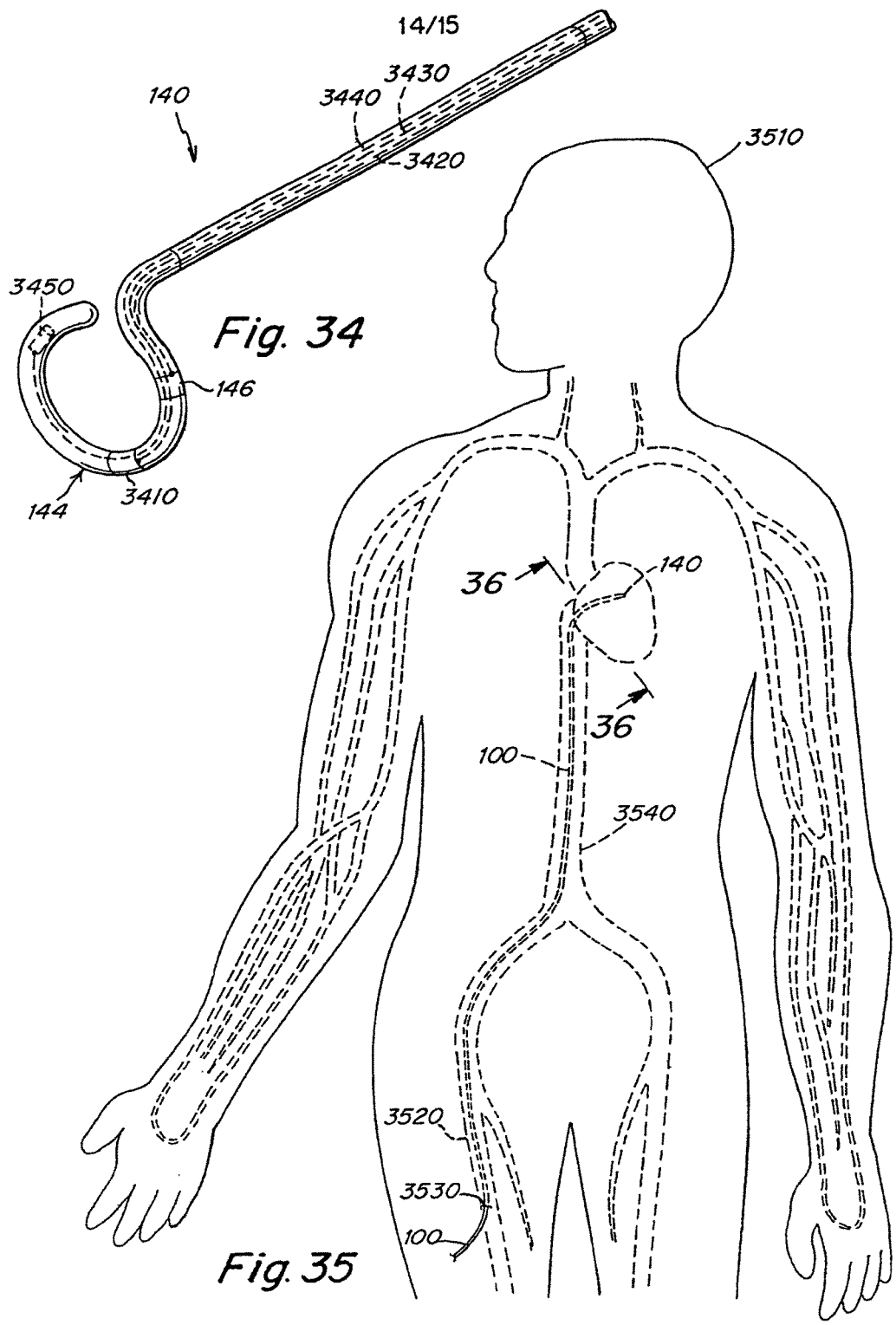
FIG. 34 is a side elevational view of a distal end tip assembly according to another embodiment of the present invention that includes a localization sensor and a temperature sensor.
FIG. 35 illustrates the insertion of a catheter of the present invention into a body of a patient.

In a further embodiment of the invention, one or more of the plurality of ring or band-type electrodes 146 may be replaced with a ring or band-shaped temperature sensor. Reference is now made to FIG. 34, which illustrates a ring-shaped ablation electrode 146 and a ring-shaped temperature sensor 3410. Temperature sensor 3410 may be a thermocouple, thermistor, or any other device for sensing temperature. The temperature sensor 3410 detects the heat of the tissue during ablation by ring or band-shaped ablation electrode 146. Temperature sensing is important during ablation because overheated tissue may explode or char, releasing debris into the bloodstream. Ablation electrode 146 is connected to connector 130 (FIG. 1) via wire 3420, which in turn connects to ablation energy generator 170; ring-shaped temperature sensor 3410 is connected to connector 130 via wire 3430, which in turn connects to controller 150. Ring-shaped electrode 146 can serve as both a reference electrode and an ablation electrode, and may be switched between applications by the controller 150 or by a human operator.

A temperature sensor or sensors, such as, but not limited to one or more thermocouples may be attached to the catheter 100 for temperature sensing during ablation procedures. The temperature sensor may be in contact with the heart tissue or, alternately, may not be in contact with the heart tissue. In other embodiments, temperature sensors may be disposed within one or more of the mapping electrodes 146, 147, for example in a hole drilled within the electrode. One skilled in the art will appreciate that more than one temperature sensor may be used in any particular configuration of catheter 100.

Localization refers to a number of techniques whereby the location of catheter 100 in a patient can be determined. Apparatus and methods for localization can be incorporated into catheter 100.

Referring again to FIG. 34, the distal end 144 of the tip assembly 140 may include an electromagnetic sensor 3450 that may be used for localization. Electromagnetic sensor 3450, may be fixed within the tip assembly 140 of the catheter 100 using any suitable mechanism, such as glue or solder. The electromagnetic sensor 3450 generates signals indicative of the location of the electromagnetic sensor. A wire 3440 electrically connects the electromagnetic sensor 3450 to the controller 150, allowing the generated signals to be transmitted to the controller 150 for processing.

In addition to the electromagnetic sensor 3450 fixed in the distal end of the tip assembly 140, a second electromagnetic sensor (not shown) may be provided that is fixed relative to the patient. The second electromagnetic sensor is attached, for example, to the patient's body, and serves as a reference sensor. A magnetic field is also provided, which is exposed to the electromagnetic sensors. Coils within each electromagnetic sensor generate electrical currents when exposed to the magnetic field. The electrical current generated by the coils of each sensor corresponds to a position of each sensor within the magnetic field. Signals generated by the reference electromagnetic sensor and electromagnetic sensor 3450 fixed to the catheter are analyzed by the controller 150 to ascertain a precise location of electromagnetic sensor 3450.

Further, the signals can be used to generate a contour map of the heart. The map may be generated by contacting the distal end 144 of the tip assembly 140 with the heart tissue at a number of locations along the heart wall. At each location, the electric signals generated by the electromagnetic sensors are transmitted to the controller 150, or to another processor, to determine and record a location of the distal end of the tip assembly. The contour map is generated by compiling the location information for each point of contact. This map may be correlated with heart signal data, measured by one or more electrodes on the distal end of the tip assembly, for each location to generate a map of both the shape and electrical activity of the heart. Signals generated by the electromagnetic sensors may also be analyzed to determine a displacement of the distal end of the tip assembly caused by heartbeat.

As an alternative to the use of electromagnetic sensors other conventional techniques, such as ultrasound or magnetic resonance imaging (MRI) can also be used for localization of tip assembly. Moreover, an impedance-based sensor can also be incorporated into the tip assembly. In an impedance-based system, several, such as three, high frequency signals are generated along different axes. The catheter electrodes may be used to sense these frequencies, and with appropriate filtering, the strength of the signal and thus the position of the catheter can be determined.

One skilled in the art will appreciate that the construction of catheter 100 may be optimized to make use of the various localization techniques.

Methods for Making the Tip Assembly

FIGS. 5-10 illustrate a number of different jigs that may be used to form a tip assembly having a fixed bend of approximately ninety degrees followed by an arcuately curved distal end. Each of these jigs may be used with a finished catheter (i.e., a catheter which is already fully assembled, and including a handle 120 and electrodes 146, 147 disposed on the distal end of the tip assembly 140), a partially finished tip assembly (i.e., a tip assembly 140 that includes electrodes 146, 147, that is not yet attached to shaft 110 and the handle 120 (FIG. 1)), or an unfinished tip assembly 140 (i.e., a tip assembly 140 without any electrodes 146, 147).

Figure 5:
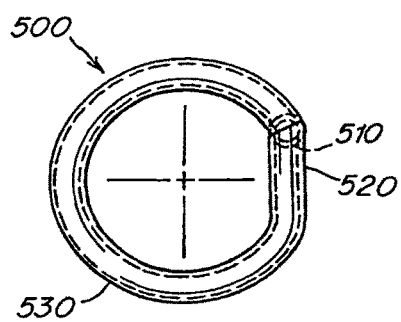
FIG. 5 illustrates a first jig that may be used to impart a fixed shape to the distal end tip assembly according to one embodiment of the present invention.
Figure 6:
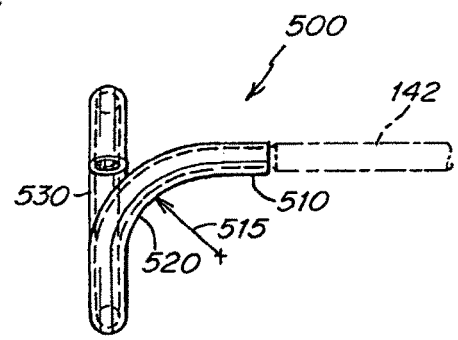
FIG. 6 illustrates a side elevational view of the jig of FIG. 5.

FIGS. 5 and 6 illustrate a first jig 500 that is formed from a hollow tube. In one embodiment, the hollow tube is formed from hypodermic stainless steel tubing, although other materials, such as a high temperature plastics such as TEFLON, DELRIN, etc., may alternatively be used. The material from which the jig 500 is formed should be thermally stable, such that its shape does not change when subjected to temperature in the range of 200-400 degrees Fahrenheit. In one embodiment, the tube used to form the jig 500 has an outer diameter of approximately 0.83 inches and an inner diameter of approximately 0.72 inches to accommodate a tip assembly 140 that is approximately 6 French in diameter, although these dimensions may be varied to accommodate different diameter tip assemblies. For example, to accommodate a tip assembly that is 10 French in diameter, a larger diameter tube would be used. As shown in FIG. 5, the distal end of the jig 500 is formed in a circle having an inner diameter of approximately 0.44 inches and an outer diameter of approximately 0.61 inches. Although the present invention is not limited to any particular dimensions, these dimensions may be used to form a tip assembly 140 in which the diameter of curvature of the distal end 144 in a resting state is approximately 20 mm. Further, and as described in more detail below, these dimensions are selected to account for a certain amount of rebounding (approximately fifteen to twenty percent) in the tip assembly 140 after removal from the jig. Although embodiments of the present invention are not limited to a tip assembly having a diameter of curvature of approximately 20 mm in a resting state, this size advantageously permits the catheter to be used for mapping and/or ablation procedures within a blood vessel, such as a pulmonary vein. It should be appreciated that for other endocardial or epicardial sites, other dimensions may be used.

As shown in FIG. 6, the jig 500 has a first straight region 510, followed by a curved region 520 having an approximately ninety degree bend relative to the straight region 510, and terminates in an arcuately shaped curved region 530 defining approximately a circle (i.e., spanning approximately 360 degrees). In one embodiment, the straight region 510 is approximately 0.125 inches in length, and the curved region 520 has an inner radius 515 of approximately 0.2 inches. It should be appreciated that other dimensions may be used to impart a different shape to the tip assembly, and to accommodate tip assemblies having a different outer diameters (e.g., a 10 French diameter tip assembly).

According to one embodiment of the present invention, the tip assembly 140 is inserted into the straight region 510 of the jig 500 and the distal end 144 of the tip assembly 140 is advanced until the very distal end of the tip assembly 140 is adjacent the distal end of the jig 500. The jig 500 and the tip assembly 140 are then heated at a predetermined temperature for a predetermined time to permanently shape the tip assembly 140. Applicants have found that heating the jig 500 and the tip assembly 140 at a temperature of approximately 200 to 400 degrees Fahrenheit for approximately thirty minutes to an hour is sufficient to permanently shape the tip assembly 140 to the desired shape. It should be appreciated that the lower the temperature, the greater amount of time is needed to permanently shape the tip assembly 140, and that the time and temperature to which the tip assembly 140 and the jig 500 are heated may vary dependent upon the materials used to form the tip assembly 140 and the jig 500. It should further be appreciated that because catheters may be sterilized prior to use or after use, the temperature to which the tip assembly 140 and the jig 500 is heated should be approximately 20 degrees Fahrenheit above the temperature at which the catheter is sterilized. This helps to prevent the tip assembly 140 from returning to its original shape during sterilization. During sterilization, a retainer may be used to hold the tip assembly 140 in the desired shape.

After heating the tip assembly 140 and the jig 500 for the predetermined time at the predetermined temperature, the tip assembly 140 and the jig 500 are allowed to cool, and the tip assembly 140 is removed from the jig 500. After removal, Applicants have found the arcuately curved distal end 144 of the tip assembly 140 tends to rebound by approximately fifteen to twenty percent, but that further rebounding at temperatures similar to those of human body temperature does not occur. Further, by modifying the materials from which the tip assembly 140 is formed, and by controlling the temperature and the time at which the tip assembly 140 is shaped, rebounding to less than three percent is expected. It should be appreciated that because a certain amount of rebounding is to be expected, the dimensions of the jig 500 should be sized to accommodate the expected amount of rebounding.

The jig of FIGS. 5 and 6 may be used to impart a desired shape to the tip assembly 140 of a finished catheter or to a partially finished tip assembly. For example, in the described embodiment, the length of the straight region 510 is relatively short to permit the tip assembly 140 of a finished catheter to be inserted into the jig 500 without damaging the electrodes 146, 147. This can be advantageous in a manufacturing setting, as finished catheters can be shaped as desired after construction and testing, and prior to shipment to an end user. This may allow fewer distinct catheters to be stocked by the manufacturer of the catheter. Alternatively, in a hospital setting, the ability to shape a finished catheter can allow fewer catheters to be stocked at the hospital, with each of the catheters being capable of being shaped as desired, prior to use.

For use with partially finished tip assemblies, the length of the straight region 510 may be lengthened, with any excess material being cut to length as desired. Moreover, with partially finished tip assemblies, the distal end of the jig 500 may form more than one complete circle, or may form a helical shape. Although the jig 500 depicted in FIGS. 5 and 6 was used to receive a tip assembly, it should be appreciated that a solid wire of a similar shape may alternatively be used. For example, the hollow stock from which the tip assembly is formed may be fed onto a solid wire having the desired shape, and then heated at an elevated temperature to produce the desired shape. The formed stock can then be removed from the wire, cut to the desired length, and finished in a conventional manner.

Figure 7:
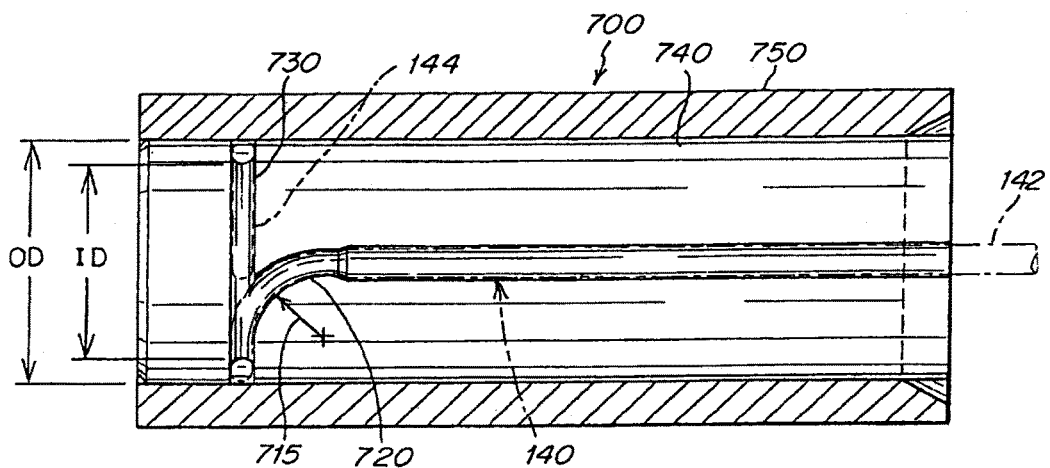
FIG. 7 is a cross sectional side view of a second jig that may be used to impart a fixed shape to the distal end tip assembly according to another embodiment of the present invention.

FIGS. 7 and 8 illustrate a second jig that may also be used to form a tip assembly having the desired shape. In particular, the jig of FIGS. 7 and 8 may be used to permanently shape the distal end of a catheter so that it includes an approximately ninety degree bend followed by an arcuately curved section. According to this embodiment, the jig 700 includes a cylindrical mandrel 740 and a cylindrical retainer 750. The cylindrical mandrel 740 and the cylindrical retainer 750 may be formed from any suitable high temperature materials, such as stainless steel, aluminum, anodized aluminum, or high temperature plastics. In one embodiment, the mandrel 740 has an outer diameter of approximately 0.75 inches and is approximately 2.5 inches long, and the retainer 750 has an inner diameter that is slightly greater than the outer diameter of the mandrel 740, so that the mandrel 740 can be fit within. Although the present invention is not limited to these dimensions, the above-identified dimensions may be used to shape the distal end tip assembly of a catheter so that it is uniquely suited for use inside a blood vessel; such as a pulmonary vein, and to accommodate an anticipated amount of rebounding after removal of the distal end tip assembly from the jig. It should be appreciated that for applications relating to other endocardial sites, other dimensions may be suitably employed.

As shown in FIGS. 7 and 8, the mandrel 740 has a passageway to receive a tip assembly 140 that includes a first straight region 710, a curved region 720 having an approximately ninety degree bend relative to the straight region 710, and an arcuately shaped curved region 730 defining a circle. The passageway may be formed in a conventional manner, for example with a milling machine. In one embodiment, the straight region 710 is approximately 1.9 inches in length, and the curved region 720 has an inner radius 715 of approximately 0.2 inches; the depth of the passageway is approximately 0.068 inches and the width is approximately the same. The described dimensions are selected to shape a tip assembly that is well suited for use within a blood vessel such as a pulmonary vein, although it should be appreciated that other dimensions may be suitably employed for use with different anatomical structures and for different applications. Again, the dimensions of the mandrel 740 and the retainer 750 should be selected to accommodate the expected amount of rebounding. In the embodiment shown, the arcuately shaped curved region 730 is spaced apart from the end of the mandrel 740 to facilitate insertion of the mandrel 740 into the retainer 750.

According to one embodiment of the present invention, a tip assembly 140 is placed into the passageway, and the mandrel 740 and the tip assembly 140 are inserted into the retainer 750. The retainer 750 acts to hold the tip assembly 140 in place within the passageway of the mandrel 740. The jig 700 and the tip assembly 140 are then heated at a predetermined temperature for a predetermined time to permanently shape the tip assembly 140 in a manner similar to that described above with respect to the first jig 500. Because of the larger thermal mass of the jig 700 relative to the jig 500, Applicants have found that a longer time may be needed to shape the tip assembly 140 than with the first jig 500, for example, about 20 additional minutes. To lessen the amount of time required to shape the tip assembly 140, the mandrel 740 may be hollowed out, for example. After heating the tip assembly 140 and the jig 700 for the predetermined time at the predetermined temperature, the tip assembly 140 and the jig 700 are allowed to cool, and then the tip assembly 140 is removed from the jig 700. As with the jig of FIGS. 5 and 6, the jig 700 may be used to impart a desired shape to the tip assembly 140 of a finished catheter or to a partially finished tip assembly. Indeed, because the tip assembly 140 is placed within the passageway rather than being threaded through it, the jig 700 is particularly well suited for use with a finished tip assembly, as damage to the finished tip assembly resulting from contact with the jig can be avoided.

FIGS. 9 and 10 illustrate another jig that may be used to form a tip assembly 140 having an approximately ninety degree bend followed by an arcuately curved distal end. According to this embodiment, the jig 900 includes a disk-shaped mandrel 940 and a circular cover 950. The disk-shaped mandrel 940 and the circular cover 950 may again be formed from any suitable high temperature materials, such as stainless steel, aluminum, anodized aluminum, or high temperature plastics. The cover 950 is removably attached to the mandrel 940 by a fastener 960, such as a threaded screw, that is passed through an aperture 980 in the cover 950. The mandrel 940 may include a threaded aperture to receive the fastener 960. Attached to the mandrel 940 is a tubular extension 970 that may be made from any suitable material, and which is attached, for example, with a high temperature epoxy or by welding to the mandrel. The tubular extension 970 may be used to support the proximal end 142 of the tip assembly 140 without substantially increasing the thermal mass of the jig 900.

As shown in FIGS. 9 and 10, the mandrel 940 has a passageway to receive a tip assembly 140 that includes a first straight region 910, a curved region 920 having an approximately ninety degree bend relative to the straight region 910, and an arcuately shaped curved region 930 defining a circle. The arcuately shaped curved region 930 may be formed by milling an annular groove in a top surface of the mandrel 940, while the straight region 910 may be formed by drilling a through hole through a section of arcuately shaped curved region 930, for example. A ninety degree bend is formed at the intersection of the annular groove and the through hole. In one embodiment, the arcuately shaped curved region 930 has an outer diameter of approximately 0.5 inches and the annular groove has a width of approximately 0.07 inches. The above-described dimensions are selected to shape the tip assembly so that it is well suited for use within a blood vessel such as a pulmonary vein, although it should be appreciated that other dimensions may be suitably employed for use with different anatomical structures and for different applications. The depth of the groove should be sufficiently greater than the outer diameter of the tip assembly 140 so that the bend in the tip assembly 140 takes place over a length of the tip assembly 140. For example, in one embodiment, the depth of the groove is approximately twice the width of the groove to avoid an immediate ninety degree bend in the tip assembly 140. Such an immediate bend could interfere with operation of the control cables that are used to adjust the radius of curvature of the distal end 144 of the tip assembly 140. Again, the dimensions of the mandrel 940 should be selected to accommodate the expected amount of rebounding, and the desired dimensions and shape of the tip assembly 140.

According to one embodiment of the present invention, a tip assembly 140 is threaded through the tubular extension 970 and the straight region 910 of the mandrel 940, and the distal end 144 of the tip assembly 140 is placed into the annular groove in the mandrel 940. The cover 950 is then fastened to the mandrel 940. The cover 950 acts to hold the tip assembly 140 in place within the passageway of the mandrel 940. The jig 900 and the tip assembly 140 are then heated at a predetermined temperature for a predetermined time to permanently shape the tip assembly 140 in a manner similar to that described above with respect to the first and second jigs. After heating the tip assembly 140 and the jig 900 for the predetermined time at the predetermined temperature, the tip assembly 140 and the jig 900 are allowed to cool, and then the tip assembly 140 is removed from the jig 900.

As with the previously described jigs 500 and 700, the jig 900 may be used to impart a desired shape to the tip assembly 140 of a finished catheter or to a partially finished tip assembly. Because the distal end of the tip assembly is inserted straight ahead into the mandrel 940, rather than along a curved path, the jig 900 is also particularly well suited for use with a finished tip assembly, as damage to the finished tip assembly resulting from contact with the jig can be avoided.

Although the jigs 500, 700, and 900 of FIGS. 5-10 have been illustrated and described as being useful in forming a tip assembly having a fixed bend of approximately ninety degrees followed by an arcuately curved distal end, it should be appreciated that each of these jigs may also be used or modified for use with a tip assembly including an active bend, such as described above with respect to FIG. 19. For example, for creating a permanent bias of a few degrees relative to the straight regions 510, 710, and 910, the approximately ninety degree bend may have a larger radius that may be varied according to the intended use of the tip assembly. As noted above with respect to FIG. 19, by permanently biasing the intermediate section 2180 (FIG. 19) away from the straight regions 510, 710, and 910, bending takes place in a known and controlled manner. Moreover, it should be appreciated that rather than terminating in a curved region 530, 730, 930 that spans approximately 360 degrees in a single plane (e.g., a circle), the curved region 530, 730, and 930 may be formed in a helical shape.

Methods of Use

As discussed above, the catheter system of the invention may be used in mapping and/or ablation applications. In one embodiment of the invention, the mapping or ablation is performed in the heart of a patient. In the mapping application, multiple signals may be received from the heart tissue via multiple electrodes on the catheter. Each electrode may measure a continuous signal (i.e., electrogram) from the heart tissue. The continuous signal may represent the voltage of the heart tissue in contact with the electrode, with respect to a reference voltage, as it changes with time. The reference voltage may be obtained using a dedicated reference electrode or another measurement electrode. The quality of the signal received by each electrode improves as both the size of the electrode and the isolation of the electrode increases.

Preferably, multiple electrodes are employed, such that multiple electrograms may be obtained simultaneously. This allows for multiple data points, which can result in a more precise mapping of the heart signal and a shorter required measurement time. A shorter measurement time advantageously reduces the x-ray exposure to patients and physicians during fluoroscopy, when employed during the catheter procedure.

The mapping function of the catheter can be used for a number of different applications. For example, in one application, the catheter may be used to measure the conductivity at various points of the septal wall, which separates the left and right sides of the heart, to determine a preferred sight for puncture of the septal wall. In another application, the conductivity of the heart tissue may be measured between adjacent electrodes in contact with the heart tissue to determine the continuity of a lesion formed by ablation. In still another application, the catheter may used to identify electrical signals within the heart that are characteristic of a number of heart conditions. For example, the focus site of an arrhythmia (e.g., atrial fibrillation, AV nodal tachycardia or tachycardia resulting from Wolff-Parkinson-White syndrome).

Reference is now made to FIG. 35, which illustrates a method of insertion of the catheter 100 into a patient 3510 in accordance with an embodiment of the present invention. The catheter 100 is inserted into the patient via a blood vessel, e.g., subclavian vein, jugular vein, or femoral vein. In FIG. 35, the catheter 100 is shown entering a femoral vein 3520 via an incision 3530 in the thigh of the patient 3510. The catheter 100 may be introduced into the vein using a sheath/dilator (not shown). The sheath/dilator may be anchored at the incision site, for example by stitching the sheath/dilator to the patient's skin at the area of incision 3530. From the incision site 3530 in the femoral vein 3520, the catheter 100 may be advanced independently, or through a sheath/dilator, up the inferior vena cava 3540 into the right atrium of the heart.

Figure 36:
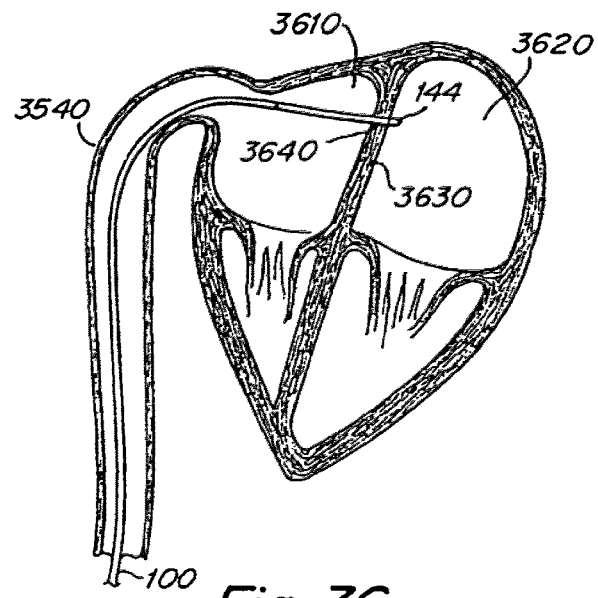
FIG. 36 illustrates the insertion of the catheter of the present invention into a heart.

Reference is now made to FIG. 36, which illustrates a diagram of a cross-sectional view of the heart taken along line A-A in FIG. 35. The catheter 100 is shown entering the right atrium 3610 via the inferior vena cava 3540. For passage of the catheter 100 into the left atrium, 3620 the distal end of the catheter 100 may be passed trans-septally through the septal wall 3630. In one method, a puncture 3640 in the septal wall 3630 is made at the foramen ovale, an area of the septal wall having a decreased thickness and decreased conductivity relative to other areas of the septal wall. As described previously, electrodes on the distal end of the catheter 100 may be used to locate the foramen ovale, or another preferred site to puncture the septal wall 3630. As shown in FIG. 36, the distal end of the tip assembly 140 of the catheter 100 traverses the septal wall 3630 from the right atrium 3610 and enters the left atrium 3620. The distal end of the catheter 100 may be used for mapping and/or ablation procedures in the left atrium 3620 or may be maneuvered into the pulmonary vein(s) for mapping and/or ablation. It should be appreciated that the catheter may also be used to perform mapping and/or ablation in the right heart, in the ventricles, or in any other area of the heart or blood vessels of the circulatory system, and that the catheter 1 need not pass through the septal wall to enter these areas.

Figure 37:
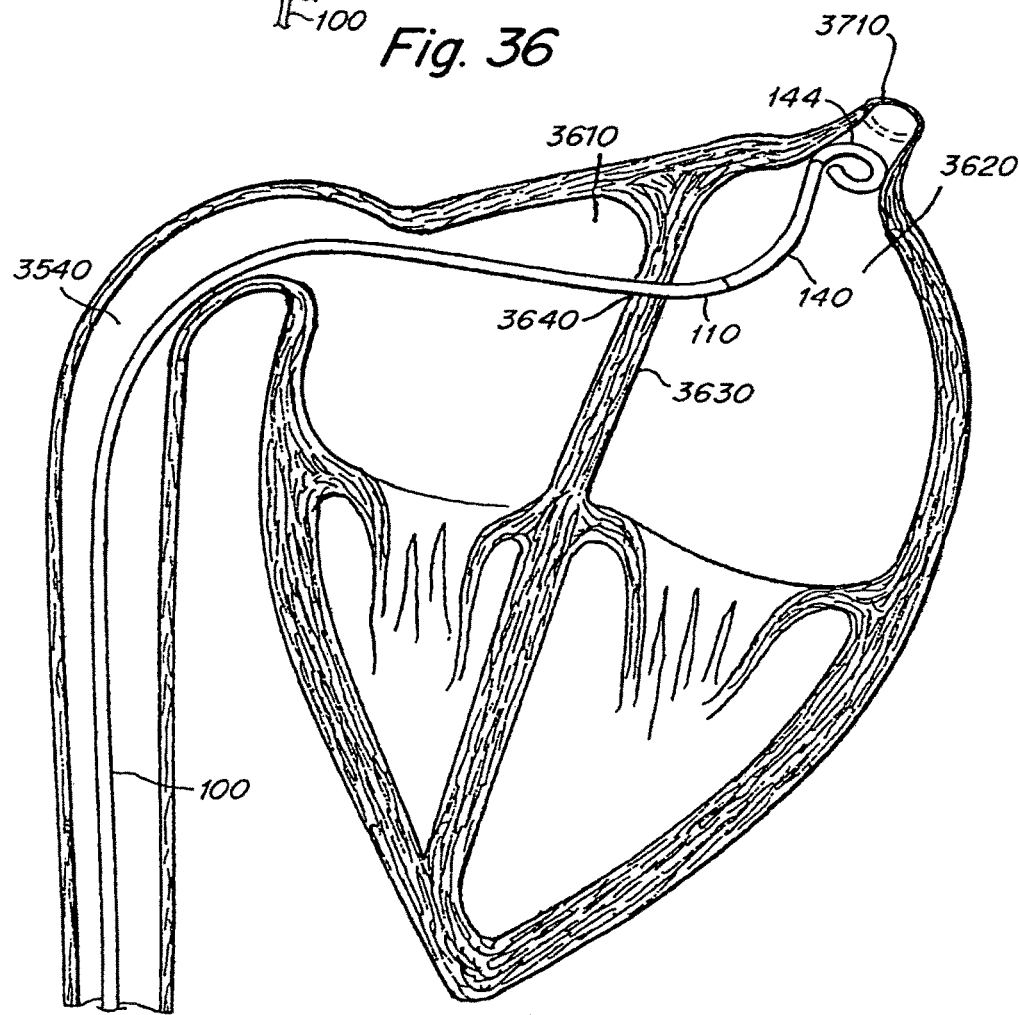
FIG. 37 illustrates the insertion of the distal end of the catheter into the ostium of a pulmonary vein in the heart.

Referring now to FIG. 37, which is an expanded view of FIG. 36, in one embodiment of the present invention, once inside the left atrium 3620, the distal end of the catheter 100 may be advanced towards the ostium of one of the pulmonary veins 3710. In this embodiment, the radius of curvature of the distal end 144 of the tip assembly 140 is remotely adjusted to snugly fit against the annular walls of the pulmonary vein 3710 by manipulation of the actuator 122, 124 (FIG. 1) that controls the radius of curvature of the distal end 144 of the tip assembly 140. In this position, the graphical indicia 3310 (FIG. 33) on the handle 120 may be used to give the user an indication of the diameter of the ostium of the pulmonary vein at this location. Mapping may be performed, as can ablation.

Because of the approximately ninety degree bend in the tip assembly 140, pressure applied to the handle 120 is translated via the shaft to force the arcuately curved distal end 144 of the tip assembly 140 tightly against the ostium of the pulmonary vein 3710. In this position, the user may also apply pressure to the actuator (e.g., the slide actuator 124) that controls the radius of curvature of the distal end 144 of the tip assembly 140 to also apply an outwardly radial pressure that further forces the distal end 144 of the tip assembly 140 tight against the ostium of the pulmonary vein 3710. Mapping may then be performed to locate a focal trigger or triggers of atrial fibrillation. It should be appreciated that the ability to force the distal end 144 of the tip assembly 140 tightly against the inner circumferential surface of a blood vessel, such as the ostium of a pulmonary vein, enhances the ability to accurately locate a focal trigger or triggers of atrial fibrillation.

Should ablation be determined to be an effective solution, ablation energy may then be provided by the ablation energy generator 170 (FIG. 1) to create a circular lesion around the circumference of the ostium of the pulmonary vein 3710. By controlling which electrodes (disposed on the distal end of the tip assembly, but not shown) are used to provide such ablation energy, a full circumferential lesion or a partial circumferential lesion may be created. Further, by monitoring of the temperature of at the site (for example, by using one or more temperature sensors disposed along the distal end 144 of the tip assembly 140), care may be exercised to ensure that charring is prevented and that the appropriate temperatures necessary for ablation are achieved. After ablation, the mapping electrodes may then be used to verify that the electrical conductivity of the tissue has been destroyed.

One advantage of using a catheter according to the invention in the described method is that only a single catheter is necessary to (1) determine the location of the foramen ovale for passage through the septal wall, (2) perform any desired mapping procedures, and (3) perform any desired ablation procedures. This avoids the need for changing catheters during procedures as between, for example, mapping and ablation procedures. It may also reduce the number of removal and reinsertion operations needed during a patient's electrophysiology study and treatment procedure. Further, because the radius of curvature of the distal end of the tip assembly may be remotely altered within the endocardial site, the catheter may be used on any sized patient from an infant or small animal to an adult or large animal, as "one size fits all." Moreover, should the size of a blood vessel or other anatomical structure be different than that which was anticipated, it is not necessary to remove the catheter and insert another more appropriately sized catheter. As noted above, this ability to be used with any sized patient can also reduce the need for a manufacturer or a care provider to stock a number of differently sized catheters.

The various configurations of the catheter illustrated in the figures are exemplary. One skilled in the art will appreciate that the number, size, orientation, and configuration of the mapping electrodes and the ablation electrodes, as well as various diameters and lengths of the catheter can be provided depending upon the particular application.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A catheter comprising:
   a handle;
   a flexible shaft having a longitudinal axis coupled to the handle;
   a tip assembly formed of more than one section that are bonded together, wherein a proximal end of the tip assembly is attached to a distal end of the flexible shaft, wherein a material of at least one section of the more than one section is less stiff than the stiffness of the flexible shaft and wherein the tip assembly includes a bend of approximately 90° relative to the longitudinal axis of the shaft, and wherein a distal end of the tip assembly includes an arcuate curve;
   a first pull cable anchored proximal to the tip assembly, the first pull cable being configured to steer the tip assembly, in a plane perpendicular to the longitudinal axis of the shaft; and
   a second pull cable anchored at the distal end of the tip assembly and configured to adjust a diameter of the arcuate curve.

2. The catheter of claim 1, wherein the second pull cable is configured to decrease the diameter of the arcuate curve when tension is applied thereto.

3. The catheter of claim 1, wherein the distal end of the tip assembly is biased in an arcuate shape.

4. The catheter of claim 1, wherein the catheter is configured such that the arcuate curve is adjustable from a diameter of approximately 5 mm to a diameter of approximately 50 mm.

5. The catheter of claim 1, further comprising: a movable electrode; and a control wire coupled to the movable electrode to enable the movable electrode to be slid along at least a portion of the distal end of the tip assembly.

6. The catheter of claim 5, wherein the movable electrode is movable between a first position and a second position on the tip assembly, the first position being spaced apart from the second position by at least 360° along the curved shape such that the movable electrode is movable to form a circular lesion.

7. The catheter of claim 5, further comprising: a cap electrode coupled to a terminal end of the tip assembly.

8. The catheter of claim 1, further comprising: a localization sensor coupled to the distal end of the tip assembly.

9. The catheter of claim 8, wherein the sensor is an electromagnetic sensor.

10. The catheter of claim 1, further comprising: an irrigation line disposed at least partially within the tip assembly.

11. A catheter comprising:
    a handle;
    a flexible shaft having a proximal end, a distal end, and a longitudinal axis, the proximal end of the flexible shaft coupled to the handle;
    a tip assembly formed of a proximal section and at least one other section that are bonded together, wherein the proximal section is attached to the distal end of the flexible shaft and has approximately the same outer diameter as the flexible shaft, and wherein the proximal section includes a bend of approximately 90° relative to the longitudinal axis of the shaft, and a distal section of the tip assembly is biased into an arcuate curve;
    a first pull cable anchored proximal to the tip assembly, the first pull cable being configured to rotate the tip assembly in a plane perpendicular to the longitudinal axis of the flexible shaft; and
    a second pull cable anchored at the distal end of the tip assembly and configured to adjust a diameter of the arcuate curve.

12. The catheter of claim 11, wherein the arcuate curve is adjustable between a diameter of about 5 mm to a diameter of about 50 mm.

13. The catheter of claim 11, wherein the tip assembly includes a cap electrode at a distal end thereof.

14. The catheter of claim 13, wherein the tip assembly includes an irrigation channel passing within the tip assembly.

15. The catheter of claim 11, wherein the tip assembly includes a localization sensor.

16. The catheter of claim 15, wherein the localization sensor is an electromagnetic sensor.

17. The catheter of claim 11, further comprising: a movable electrode; and a control wire coupled to the movable electrode, the control wire being actuatable to effect movement of the movable electrode along the tip assembly.

18. The catheter of claim 17, wherein the movable electrode is movable between a first position and a second position along the tip assembly, the first position being spaced apart from the second position by at least 360° along the arcuate curve of the tip assembly such that the movable electrode is movable to form a circular lesion.

19. A catheter comprising:
    a handle;
    a flexible shaft having a longitudinal axis coupled to the handle;
    a tip assembly formed of a proximal section, an intermediate section and a distal section that are bonded together, wherein the proximal section is attached to a distal end of the flexible shaft, wherein the intermediate section has a diameter that is smaller than the diameter of the proximal section and wherein the proximal section includes a bend of approximately 90° relative to the longitudinal axis of the shaft, and a distal end of the tip assembly including an arcuate curve;
    a first cable anchored proximal to the tip assembly, the first cable being configured to steer the tip assembly in a plane perpendicular to the longitudinal axis of the shaft; and
    a second cable anchored at the distal end of the tip assembly and configured to adjust a diameter of the arcuate curve.

20. The catheter of claim 19, wherein a portion of the tip assembly is inserted into the flexible shaft and wherein the first cable and the second cable are push cables.

* * * * *